(12) United States Patent
Sagt et al.

(10) Patent No.: US 7,968,312 B2
(45) Date of Patent: Jun. 28, 2011

(54) PRODUCTION OF POLYPEPTIDES BY IMPROVED SECRETION

(75) Inventors: Cornelis Maria Jacobus Sagt, Utrecht (NL); Nöel Nicolaas Maria Elisabeth Van Peij, Delft (NL); Linda De Lange, Delfgauw (NL); Martina Beishuizen, Rotterdam (NL); Serge Petrus Donkers, Hellevoetsluis (NL)

(73) Assignee: DSM IP Assets B.V., Te Heerlen (NL)

( * ) Notice: Subject to any disclaimer, the term of this patent is extended or adjusted under 35 U.S.C. 154(b) by 537 days.

(21) Appl. No.: 11/629,882

(22) PCT Filed: Jun. 16, 2005

(86) PCT No.: PCT/EP2005/052805
§ 371 (c)(1),
(2), (4) Date: Nov. 2, 2007

(87) PCT Pub. No.: WO2005/123763
PCT Pub. Date: Dec. 29, 2005

(65) Prior Publication Data
US 2009/0004693 A1 Jan. 1, 2009

(30) Foreign Application Priority Data
Jun. 16, 2004 (EP) .................................. 04076775

(51) Int. Cl.
C12P 21/06 (2006.01)
C12N 15/00 (2006.01)
C12N 1/00 (2006.01)
C07H 21/04 (2006.01)

(52) U.S. Cl. ................. 435/69.1; 435/320.1; 435/252.3; 435/254.11; 536/23.1; 536/23.74

(58) Field of Classification Search .................. None
See application file for complete search history.

(56) References Cited

U.S. PATENT DOCUMENTS
6,344,341 B1  2/2002 Keranen et al.
2003/0119013 A1 6/2003 Jiang et al.
2004/0025202 A1 2/2004 Laurie et al.

FOREIGN PATENT DOCUMENTS
WO 99/02716 1/1999
WO 02/086090 10/2002
WO 2004/067709 8/2004

OTHER PUBLICATIONS

International Search Report for PCT/EP2005/052805 mailed Nov. 8, 2005.
Cao et al. "The general protein secretory pathway: Phylogenetic analyses leading to evolutionary conclusions" Biochim. Biophys. Acta 1609:115-125 (Jan. 2003).
Conesa et al. "The secretion pathway in filamentous fungi: A biotechnological view" Fungal Gen. Biol. 33:155-171 (2001).
Gouka et al. "Efficient production of secreted proteins by *Aspergillus*: Progress, limitations and prospects" Appl. Microbiol. Biotechnol. 47:1-11 (1997).
Punt et al. "Filamentous fungi as cell factories for heterologous protein production" Trends in Biotechnol. 20:200-206 (2002).
UniProtKB "Hypothetical protein" Database Accession No. Q5AVF9 (May 2005).
UniProtKB "Protein transport protein SEC61 alpha subunit" Database Accession No. SC61A_NEUCR (Oct. 2004).
UniProtKB "Putative SEC61 (Fragment)" Database Accession No. Q6UP01 (Jul. 2004).
Valkonen et al. "Improvement of foreign-protein production in *Aspergillus niger* var. *awamori* by constitutive induction of the unfolded-protein response" Appl. Environ. Microbiol. 69:6979-6986 (Dec. 2003).

*Primary Examiner* — David J Steadman
(74) *Attorney, Agent, or Firm* — Nixon & Vanderhye, PC

(57) ABSTRACT

The present invention relates to polypeptides that have an activity corresponding to at least one activity of the SEC61 polypeptide, polynucleotides encoding these polypeptides and the use thereof in the preparation of host cells suitable for production of a polypeptide of interest. Such host cells may have an increased capacity to secrete a polypeptide of interest.

18 Claims, 10 Drawing Sheets

SEQUENCE LISTING

```
<160> NUMBER OF SEQ ID NOS: 23

<210> SEQ ID NO 1
<211> LENGTH: 2220
<212> TYPE: DNA
<213> ORGANISM: Aspergillus niger
<220> FEATURE:
<221> NAME/KEY: exon
<222> LOCATION: (181)..(190)
<223> OTHER INFORMATION: exon
<220> FEATURE:
<221> NAME/KEY: Intron
```

```
<222> LOCATION: (191)..(279)
<223> OTHER INFORMATION: Intron
<220> FEATURE:
<221> NAME/KEY: exon
<222> LOCATION: (280)..(380)
<223> OTHER INFORMATION: exon
<220> FEATURE:
<221> NAME/KEY: Intron
<222> LOCATION: (381)..(438)
<223> OTHER INFORMATION: Intron
<220> FEATURE:
<221> NAME/KEY: exon
<222> LOCATION: (439)..(606)
<223> OTHER INFORMATION: exon
<220> FEATURE:
<221> NAME/KEY: Intron
<222> LOCATION: (607)..(678)
<223> OTHER INFORMATION: Intron
<220> FEATURE:
<221> NAME/KEY: exon
<222> LOCATION: (679)..(1754)
<223> OTHER INFORMATION: exon
<220> FEATURE:
<221> NAME/KEY: Intron
<222> LOCATION: (1755)..(1811)
<223> OTHER INFORMATION: Intron
<220> FEATURE:
<221> NAME/KEY: exon
<222> LOCATION: (1812)..(1893)
<223> OTHER INFORMATION: exon

<400> SEQUENCE: 1
```

| | | | | | |
|---|---|---|---|---|---|
| catcgcttcc | tcccttctc | ctccatcctc | tctctcttcc | gtcgtctttt | cttcttctcc | 60 |
| ttctcctttt | gtacttcccc | tccattcctt | cagctggttc | tcgcctccag | ctttcctttc | 120 |
| tttctttccc | tccccttta | ttcgagtaat | cctgcagctc | tgggaggtgc | aacagtcaca | 180 |
| atgagcggac | gtgagtcttg | cacgcgatcg | ctgccatctc | cgcgacagcg | ttccatcctt | 240 |
| tacctcaatg | gatcagcaaa | tgctgatact | cgattctagt | ccggtttctc | gatctcatca | 300 |
| agcccttcac | gccctcctc | ccggaggtgg | ccgccccgga | aaccaaggtt | cccttcaacc | 360 |
| agaagttgat | gtggacgggg | gtacgtgata | cttgtccagc | tcgacatgag | cttctaagct | 420 |
| aatggattac | ccctgcagtt | gaccctattg | atcttcctgg | tcatgagcca | gatgcccttg | 480 |
| tacggaattg | tctcctctga | cacctccgac | cctctgtact | ggctccgtat | gatgttggcc | 540 |
| agtaaccggg | gtaccctgat | ggaactgggt | atcacccca | tcatctcctc | tggcatggtt | 600 |
| ttccaggtat | gtaatgggga | aattgcaatc | tgatcacgga | tatcgggcat | ttgctaatat | 660 |
| gtggcttttg | tctgatagct | ctcgctggt | acccacctca | tcgatgtcaa | cctggacctg | 720 |
| aagaccgacc | gtgaactgta | tcagaccgct | cagaagctct | tcgctatcat | cctgtccttc | 780 |
| ggtcaggcct | gcgtctacgt | cctcactggt | ctttacggcc | agcccagtga | ccttggtgcc | 840 |
| ggtatctgtg | ttctgctgat | tgttcagctg | gtcgttgctg | gcttggttgt | catcctgctg | 900 |
| gatgagctgc | tccagaaggg | ctatggtctt | ggtagcggta | tctctctgtt | catcgcgacc | 960 |
| aacatctgcg | agtcgatcgt | ctggaaggct | ttctctccta | cgaccatcaa | cactggccgt | 1020 |
| ggtcccgagt | ttgagggtgc | catcattgcc | ctcttccacc | ttctgttgac | ctggtccgac | 1080 |
| aagcagcgcg | ctctccgcga | ggcttttctac | cgccagaacc | tccccaacat | catgaacctg | 1140 |
| ctggctactc | tcctcgtttt | cgccgctgtg | atctacctcc | agggcttccg | tgttgagatc | 1200 |
| cctgtcaagt | cctcccgcca | gcgtggcatg | cgtggttcct | accctgttcg | cctgttctac | 1260 |
| acctccaaca | tgcccatcat | gcttcagtct | gctctgtgct | ccaacatctt | cctcatcagt | 1320 |
| cagatgctgt | actctcgctt | ctctgacaac | tccttgtca | agcttctcgg | tgtttgggag | 1380 |
| cctcgtgagg | gttctgccca | gctccacgcc | gcctccggca | ttgcctacta | catgtctcct | 1440 |

```
cccctgaact tcaaggaggc ccttcttgac cccattcaca ccgccgttta catcaccttc    1500
atgctggttg cttgtgctct cttctccaag acctggattg aggtttccgg ctctgctccc    1560
cgcgatgttg ccaagcagct caaggaccag ggtctcgtga tggctggtca ccgtgagcag    1620
agcatgtaca aggagctcaa gcgcgtcatc cctactgctg ctgctttcgg tggtgcctgc    1680
attggtgccc tgtccgtcgc ttctgacctg cttggtgctc ttggcagcgg tactggtatc    1740
ctccttgccg ttacgtaagt cttcactttg gtctcagatt ttctgaagtg gatactaaca    1800
ttcaaatgca ggattatata cggatacttt gaaattgccg cccgtgaggg cgacattgga    1860
tcgggcctca agggccttgt tccgggtaac tagataaggc ccccttttg atgaaagcat     1920 gagaagaagt ttgagggctt atgtttgttc ttgcaacttt ctgtttcttc tcaggtagtg    1980
tgctgttgtg gctgggatct ggattattta gtttcttgat ggatgtatgg ctagttttaa    2040
caatttgcag gaggggaaga tcttctctac ggagatacgt ccacgccaca gctgtacata    2100
gcacctacct ggtttgtaac catattgaca aaagatctaa aattaactta attggcttga    2160
ccatctcggg tgtctttcta ctccaactgc aaggggtgtc tgataaatct ctatactagg    2220

<210> SEQ ID NO 2
<211> LENGTH: 1437
<212> TYPE: DNA
<213> ORGANISM: Aspergillus niger

<400> SEQUENCE: 2
atgagcggac tccggtttct cgatctcatc aagcccttca cgcccctcct cccggaggtg      60
gccgccccgg aaaccaaggt tcccttcaac cagaagttga tgtggacggg gttgacccta     120
ttgatcttcc tggtcatgag ccagatgccc ttgtacggaa ttgtctcctc tgacacctcc     180
gaccctctgt actggctccg tatgatgttg gccagtaacc ggggtaccct gatggaactg     240
ggtatcaccc ccatcatctc ctctggcatg gtttttccagc ttctcgctgg tacccacctc     300
atcgatgtca acctggacct gaagaccgac cgtgaactgt atcagaccgc tcagaagctc      360
ttcgctatca tcctgtcctt cggtcaggcc tgcgtctacg tcctcactgg tctttacggc      420
cagcccagtg accttggtgc cggtatctgt gttctgctga ttgttcagct ggtcgttgct      480
ggcttggttg tcatcctgct ggatgagctg ctccagaagg gctatggtct tggtagcggt      540
atctctctgt tcatcgcgac caacatctgc gagtcgatcg tctggaaggc tttctctcct      600
acgaccatca acactggccg tgtcccgag tttgagggtg ccatcattgc cctcttccac       660
cttctgttga cctggtccga caagcagcgc gctctccgcg aggctttcta ccgccagaac      720
ctccccaaca tcatgaacct gctggctact ctcctcgttt cgccgctgt gatctacctc       780 cagggcttcc gtgttgagat ccctgtcaag tcctcccgcc agcgtggcat gcgtggttcc      840
taccctgttc gcctgttcta cacctccaac atgcccatca tgcttcagtc tgctctgtgc      900
tccaacatct tcctcatcag tcagatgctg tactctcgct tctctgacaa cctccttgtc     960
aagcttctcg tgtttggga gcctcgtgag ggttctgccc agctcacgc cgcctccggc      1020 attgcctact acatgtctcc tccccctgaac ttcaaggagg cccttcttga ccccattcac    1080
accgccgttt acatcacctt catgctggtt gcttgtgctc tcttctccaa gacctggatt     1140
gaggtttccg gctctgctcc ccgcgatgtt gccaagcagc tcaaggacca gggtctcgtg     1200
atggctggtc accgtgagca gagcatgtac aaggagctca gcgcgtcat ccctactgct      1260 gctgctttcg gtggtgcctg cattggtgcc ctgtccgtcg cttctgacct gcttggtgct    1320
cttggcagcg gtactggtat cctccttgcc gttacgatta tacggata ctttgaaatt      1380
```

```
gccgcccgtg agggcgacat tggatcgggc ctcaagggcc ttgttccggg taactag      1437
```

<210> SEQ ID NO 3
<211> LENGTH: 478
<212> TYPE: PRT
<213> ORGANISM: Aspergillus niger

<400> SEQUENCE: 3

```
Met Ser Gly Leu Arg Phe Leu Asp Leu Ile Lys Pro Phe Thr Pro Leu
1               5                   10                  15

Leu Pro Glu Val Ala Ala Pro Glu Thr Lys Val Pro Phe Asn Gln Lys
            20                  25                  30

Leu Met Trp Thr Gly Leu Thr Leu Leu Ile Phe Leu Val Met Ser Gln
        35                  40                  45

Met Pro Leu Tyr Gly Ile Val Ser Ser Asp Thr Ser Asp Pro Leu Tyr
    50                  55                  60

Trp Leu Arg Met Met Leu Ala Ser Asn Arg Gly Thr Leu Met Glu Leu
65                  70                  75                  80

Gly Ile Thr Pro Ile Ile Ser Ser Gly Met Val Phe Gln Leu Leu Ala
                85                  90                  95

Gly Thr His Leu Ile Asp Val Asn Leu Asp Leu Lys Thr Asp Arg Glu
            100                 105                 110

Leu Tyr Gln Thr Ala Gln Lys Leu Phe Ala Ile Ile Leu Ser Phe Gly
        115                 120                 125

Gln Ala Cys Val Tyr Val Leu Thr Gly Leu Tyr Gly Gln Pro Ser Asp
    130                 135                 140

Leu Gly Ala Gly Ile Cys Val Leu Leu Ile Val Gln Leu Val Val Ala
145                 150                 155                 160

Gly Leu Val Val Ile Leu Leu Asp Glu Leu Leu Gln Lys Gly Tyr Gly
                165                 170                 175

Leu Gly Ser Gly Ile Ser Leu Phe Ile Ala Thr Asn Ile Cys Glu Ser
            180                 185                 190

Ile Val Trp Lys Ala Phe Ser Pro Thr Thr Ile Asn Thr Gly Arg Gly
        195                 200                 205

Pro Glu Phe Glu Gly Ala Ile Ile Ala Leu Phe His Leu Leu Leu Thr
    210                 215                 220

Trp Ser Asp Lys Gln Arg Ala Leu Arg Glu Ala Phe Tyr Arg Gln Asn
225                 230                 235                 240

Leu Pro Asn Ile Met Asn Leu Leu Ala Thr Leu Leu Val Phe Ala Ala
                245                 250                 255

Val Ile Tyr Leu Gln Gly Phe Arg Val Glu Ile Pro Val Lys Ser Ser
            260                 265                 270

Arg Gln Arg Gly Met Arg Gly Ser Tyr Pro Val Arg Leu Phe Tyr Thr
        275                 280                 285

Ser Asn Met Pro Ile Met Leu Gln Ser Ala Leu Cys Ser Asn Ile Phe
    290                 295                 300

Leu Ile Ser Gln Met Leu Tyr Ser Arg Phe Ser Asp Asn Leu Leu Val
305                 310                 315                 320

Lys Leu Leu Gly Val Trp Glu Pro Arg Glu Gly Ser Ala Gln Leu His
                325                 330                 335

Ala Ala Ser Gly Ile Ala Tyr Tyr Met Ser Pro Leu Asn Phe Lys
            340                 345                 350

Glu Ala Leu Leu Asp Pro Ile His Thr Ala Val Tyr Ile Thr Phe Met
        355                 360                 365
```

-continued

| | | | | | | | | | | | |
|---|---|---|---|---|---|---|---|---|---|---|---|
|Leu|Val|Ala|Cys|Ala|Leu|Phe|Ser|Lys|Thr|Trp|Ile|Glu|Val|Ser|Gly|
| |370| | | |375| | | |380| | | | | | |

Ser Ala Pro Arg Asp Val Ala Lys Gln Leu Lys Asp Gln Gly Leu Val
385             390             395                 400

Met Ala Gly His Arg Glu Gln Ser Met Tyr Lys Glu Leu Lys Arg Val
            405                 410                 415

Ile Pro Thr Ala Ala Ala Phe Gly Gly Ala Cys Ile Gly Ala Leu Ser
                420             425             430

Val Ala Ser Asp Leu Leu Gly Ala Leu Gly Ser Gly Thr Gly Ile Leu
            435             440             445

Leu Ala Val Thr Ile Ile Tyr Gly Tyr Phe Glu Ile Ala Ala Arg Glu
        450             455             460

Gly Asp Ile Gly Ser Gly Leu Lys Gly Leu Val Pro Gly Asn
465             470             475

<210> SEQ ID NO 4
<211> LENGTH: 1713
<212> TYPE: DNA
<213> ORGANISM: Aspergillus niger

<400> SEQUENCE: 4

```
atgagcggac gtgagtcttg cacgcgatcg ctgccatctc cgcgacagcg ttccatcctt      60
tacctcaatg gatcagcaaa tgctgatact cgattctagt ccggtttctc gatctcatca     120
agcccttcac gccctcctc ccggaggtgg ccgccccgga aaccaaggtt cccttcaacc     180
agaagttgat gtggacgggg gtacgtgata cttgtccagc tcgacatgag cttctaagct     240
aatggattac ccctgcagtt gaccctattg atcttcctgg tcatgagcca gatgcccttg     300
tacggaattg tctcctctga cacctccgac cctctgtact ggctccgtat gatgttggcc     360
agtaaccggg gtaccctgat ggaactgggt atcaccccca tcatctcctc tggcatggtt     420
ttccaggtat gtaatgggga aattgcaatc tgatcacgga tatcgggcat ttgctaatat     480
gtggcttttg tctgatagct tctcgctggt acccacctca tcgatgtcaa cctggacctg     540
aagaccgacc gtgaactgta tcagaccgct cagaagctct tcgctatcat cctgtccttc     600
ggtcaggcct gcgtctacgt cctcactggt ctttacggcc agcccagtga ccttggtgcc     660
ggtatctgtg ttctgctgat tgttcagctg gtcgttgctg gcttggttgt catcctgctg     720
gatgagctgc tccagaaggg ctatggtctt ggtagcggta tctctctgtt catcgcgacc     780
aacatctgcg agtcgatcgt ctggaaggct ttctctccta cgaccatcaa cactggccgt     840
ggtcccgagt ttgagggtgc catcattgcc ctcttccacc ttctgttgac ctggtccgac     900
aagcagcgcg ctctccgcga ggctttctac cgccagaacc tccccaacat catgaacctg     960
ctggctactc tcctcgtttt cgccgctgtg atctacctcc agggcttccg tgttgagatc    1020
cctgtcaagt cctcccgcca gcgtggcatg cgtggttcct accctgttcg cctgttctac    1080
acctccaaca tgcccatcat gcttcagtct gctctgtgct ccaacatctt cctcatcagt    1140
cagatgctgt actctcgctt ctctgacaac ctccttgtca agcttctcgg tgtttgggag    1200
cctcgtgagg gttctgccca gctccacgcc gcctccggca ttgcctacta catgtctcct    1260
cccctgaact tcaaggaggc ccttcttgac cccattcaca ccgccgttta catcaccttc    1320
atgctggttg cttgtgctct cttctggaag acctggattg aggtttccgg ctctgctccc    1380
cgcgatgttg ccaagcagct caaggaccag ggtctcgtga tggctggtca ccgtgagcag    1440
agcatgtaca aggagctcaa gcgcgtcatc cctactgctg ctgctttcgg tggtgcctgc    1500
attggtgccc tgtccgtcgc ttctgacctg cttggtgctc ttggcagcgg tactggtatc    1560
```

```
ctccttgccg ttacgtaagt cttcactttg gtctcagatt ttctgaagtg gatactaaca    1620
ttcaaatgca ggattatata cggatacttt gaaattgccg cccgtgaggg cgacattgga    1680
tcgggcctca agggccttgt tccgggtaac tag                                 1713
```

<210> SEQ ID NO 5
<211> LENGTH: 1437
<212> TYPE: DNA
<213> ORGANISM: Aspergillus niger

<400> SEQUENCE: 5

```
atgagcggac tccggtttct cgatctcatc aagcccttca cgcccctcct cccggaggtg      60
gccgccccgg aaaccaaggt tcccttcaac cagaagttga tgtggacggg gttgacccta     120
ttgatcttcc tggtcatgag ccagatgccc ttgtacggaa ttgtctcctc tgacacctcc     180
gaccctctgt actggctccg tatgatgttg gccagtaacc ggggtaccct gatggaactg     240
ggtatcaccc ccatcatctc ctctggcatg gttttccagc ttctcgctgg tacccacctc     300
atcgatgtca acctggacct gaagaccgac cgtgaactgt atcagaccgc tcagaagctc     360
ttcgctatca tcctgtcctt cggtcaggcc tgcgtctacg tcctcactgg tctttacggc     420
cagcccagtg accttggtgc cggtatctgt gttctgctga ttgttcagct ggtcgttgct     480
ggcttggttg tcatcctgct ggatgagctg ctccagaagg gctatggtct tggtagcggt     540
atctctctgt tcatcgcgac caacatctgc gagtcgatcg tctggaaggc tttctctcct     600
acgaccatca cactggccg tggtcccgag tttgagggtg ccatcattgc cctcttccac     660
cttctgttga cctggtccga caagcagcgc gctctccgcg aggctttcta ccgccagaac     720
ctccccaaca tcatgaacct gctggctact ctcctcgttt cgccgctgt gatctacctc     780 cagggcttcc gtgttgagat ccctgtcaag tcctcccgcc agcgtggcat gcgtggttcc     840
taccctgttc gcctgttcta cacctccaac atgcccatca tgcttcagtc tgctctgtgc     900
tccaacatct tcctcatcag tcagatgctg tactctcgct tctctgacaa cctccttgtc     960
aagcttctcg tgtttgggca gcctcgtgag ggttctgccc agctccacgc cgcctccggc    1020
attgcctact acatgtctcc tcccctgaac ttcaaggagg cccttcttga ccccattcac    1080
accgccgttt acatcacctt catgctggtt gcttgtgctc tcttctggaa gacctggatt    1140
gaggtttccg gctctgctcc ccgcgatgtt gccaagcagc tcaaggacca gggtctcgtg    1200
atggctggtc accgtgagca gagcatgtac aaggagctca gcgcgtcat ccctactgct    1260 gctgctttcg gtggtgcctg cattggtgcc ctgtccgtcg cttctgacct gcttggtgct    1320
cttggcagcg gtactggtat cctccttgcc gttacgatta tatacggata ctttgaaatt    1380
gccgcccgtg agggcgacat tggatcgggc ctcaagggcc ttgttccggg taactag       1437
```

<210> SEQ ID NO 6
<211> LENGTH: 478
<212> TYPE: PRT
<213> ORGANISM: Aspergillus niger

<400> SEQUENCE: 6

```
Met Ser Gly Leu Arg Phe Leu Asp Leu Ile Lys Pro Phe Thr Pro Leu
1               5                   10                  15

Leu Pro Glu Val Ala Ala Pro Glu Thr Lys Val Pro Phe Asn Gln Lys
            20                  25                  30

Leu Met Trp Thr Gly Leu Thr Leu Leu Ile Phe Leu Val Met Ser Gln
        35                  40                  45
```

```
Met Pro Leu Tyr Gly Ile Val Ser Ser Asp Thr Ser Asp Pro Leu Tyr
 50                  55                  60

Trp Leu Arg Met Met Leu Ala Ser Asn Arg Gly Thr Leu Met Glu Leu
 65                  70                  75                  80

Gly Ile Thr Pro Ile Ile Ser Ser Gly Met Val Phe Gln Leu Leu Ala
                 85                  90                  95

Gly Thr His Leu Ile Asp Val Asn Leu Asp Leu Lys Thr Asp Arg Glu
                100                 105                 110

Leu Tyr Gln Thr Ala Gln Lys Leu Phe Ala Ile Ile Leu Ser Phe Gly
            115                 120                 125

Gln Ala Cys Val Tyr Val Leu Thr Gly Leu Tyr Gly Gln Pro Ser Asp
        130                 135                 140

Leu Gly Ala Gly Ile Cys Val Leu Leu Ile Val Gln Leu Val Val Ala
145                 150                 155                 160

Gly Leu Val Val Ile Leu Leu Asp Glu Leu Leu Gln Lys Gly Tyr Gly
                165                 170                 175

Leu Gly Ser Gly Ile Ser Leu Phe Ile Ala Thr Asn Ile Cys Glu Ser
            180                 185                 190

Ile Val Trp Lys Ala Phe Ser Pro Thr Thr Ile Asn Thr Gly Arg Gly
        195                 200                 205

Pro Glu Phe Glu Gly Ala Ile Ile Ala Leu Phe His Leu Leu Leu Thr
    210                 215                 220

Trp Ser Asp Lys Gln Arg Ala Leu Arg Glu Ala Phe Tyr Arg Gln Asn
225                 230                 235                 240

Leu Pro Asn Ile Met Asn Leu Leu Ala Thr Leu Leu Val Phe Ala Ala
                245                 250                 255

Val Ile Tyr Leu Gln Gly Phe Arg Val Glu Ile Pro Val Lys Ser Ser
            260                 265                 270

Arg Gln Arg Gly Met Arg Gly Ser Tyr Pro Val Arg Leu Phe Tyr Thr
        275                 280                 285

Ser Asn Met Pro Ile Met Leu Gln Ser Ala Leu Cys Ser Asn Ile Phe
    290                 295                 300

Leu Ile Ser Gln Met Leu Tyr Ser Arg Phe Ser Asp Asn Leu Leu Val
305                 310                 315                 320

Lys Leu Leu Gly Val Trp Glu Pro Arg Glu Gly Ser Ala Gln Leu His
                325                 330                 335

Ala Ala Ser Gly Ile Ala Tyr Tyr Met Ser Pro Pro Leu Asn Phe Lys
            340                 345                 350

Glu Ala Leu Leu Asp Pro Ile His Thr Ala Val Tyr Ile Thr Phe Met
        355                 360                 365

Leu Val Ala Cys Ala Leu Phe Trp Lys Thr Trp Ile Glu Val Ser Gly
    370                 375                 380

Ser Ala Pro Arg Asp Val Ala Lys Gln Leu Lys Asp Gln Gly Leu Val
385                 390                 395                 400

Met Ala Gly His Arg Glu Gln Ser Met Tyr Lys Glu Leu Lys Arg Val
                405                 410                 415

Ile Pro Thr Ala Ala Phe Gly Gly Ala Cys Ile Gly Ala Leu Ser
            420                 425                 430

Val Ala Ser Asp Leu Leu Gly Ala Leu Gly Ser Gly Thr Gly Ile Leu
        435                 440                 445

Leu Ala Val Thr Ile Ile Tyr Gly Tyr Phe Glu Ile Ala Ala Arg Glu
    450                 455                 460

Gly Asp Ile Gly Ser Gly Leu Lys Gly Leu Val Pro Gly Asn
465                 470                 475
```

<210> SEQ ID NO 7
<211> LENGTH: 1800
<212> TYPE: DNA
<213> ORGANISM: Penicillium chrysogenum

<400> SEQUENCE: 7

| | | | | | |
|---|---|---|---|---|---|
| aagatagcca | ccatgagcgg | ccgtgagttc | cccgaatcct | cgtcgcgcac | gcaatcgcaa | 60 |
| caatccgtgt | cgaatcaccc | tcaattgatg | gtcaaatgct | gatggaggac | tatagtacgc | 120 |
| ttccttgact | tgatcaagcc | ctttacgccc | ctcctcccgg | aggtggcagc | tcctgagacc | 180 |
| aaggtgccct | tcaaccagaa | gttgatgtgg | actggtgtat | gtcgccctga | atccgctgtc | 240 |
| tccgcgcgaa | gtcggcttga | atcctaattg | aaacatatta | cagttgactt | tgatgatctt | 300 |
| cctggtcatg | agtcagatgc | ctctttacgg | tattgtctcc | tccgacactt | cggaccccct | 360 |
| gtactggctc | cgtatgatgc | tggccagtaa | ccggggtact | ctgatggagc | tgggtatcac | 420 |
| ccctattatc | tcctccggca | tggtcttcca | ggtatgcgat | tcacaacttt | ctcctatcac | 480 |
| catttgcgat | aattatattg | acacaacttg | ttctccagct | ccttgccggt | acccacctca | 540 |
| ttgatgtcaa | cctcgacttg | aagaccgacc | gcgagctcta | ccagaccgcc | cagaagctct | 600 |
| tcgctatcat | tctctcattc | ggccaggcct | gtgtttacgt | cctgactggt | ctctacggcc | 660 |
| agcccagtga | cctcggtgcc | ggtatctgtg | ttctcctgat | tgtccagctc | gttgtggccg | 720 |
| gtctcgtcgt | cattctgctt | gacgagctcc | tccagaaggg | ctacggtctg | gcagcggta | 780 |
| tctccctgtt | cattgccacc | aacatttgcg | agtccattgt | ctggaaggct | ttctccccca | 840 |
| ccaccatcaa | caccggccgt | ggccccgagt | tcgagggtgc | tatcatcgct | ctgttccacc | 900 |
| ttctcctgac | ctggcccgat | aagcagcgcg | ccctgtacga | ggcgttctac | cgccagaacc | 960 |
| tgcccaacgt | catgaacctc | ctggctactc | ttctggtctt | cgccgctgtc | atctacctgc | 1020 |
| agggcttccg | tgttgagatc | cccgtcaagt | cctcccgcca | gcgtggcatg | cgcggctcgt | 1080 |
| accccgtccg | cctcttctac | acctccaaca | tgcccatcat | gctccagtcc | gcgctgtgct | 1140 |
| ccaacatctt | cctcatcagt | cagatgctgt | actctcgctt | ctctgagaac | atcctggtcc | 1200 |
| agctccttgg | agtttgggag | cccgtgaggg | gatctgctca | gctttacgcc | gcctctggta | 1260 |
| ttgcttacta | catgtcacct | cctctcaact | tcaaggaggc | tcttctcgac | cccatccaca | 1320 |
| ccgctgtcta | cattaccttc | atgcttgttg | cctgcgctct | cttctccaag | acctggattg | 1380 |
| aggtttccgg | ctccgctccc | cgcgacgttg | ctaagcagct | caaggaccag | ggtcttgtca | 1440 |
| tgtctggtca | ccgtgagcag | agcatgtaca | aggagctgaa | gcgcgttatc | cctactgccg | 1500 |
| ctgctttcgg | tggtgcctgc | attggtggcc | tgtccgtcgc | ctccgacctt | atgggtgctc | 1560 |
| tcggcagtgg | tactggtatt | cttcttgccg | ttacgtaagt | tatcccgttt | gacatctcaa | 1620 |
| atatgttcat | ctcagctaac | agcttaatac | agcatcatct | acggctactt | tgaaattgcc | 1680 |
| gcccgtgagg | gtgacattgg | cgctggcctc | aagggcctcg | tccccggcag | ctaaacgaga | 1740 |
| ctgtccgtaa | tttcacgagc | agcatgacat | aggatcacac | cggtcctttg | caacctctct | 1800 |

<210> SEQ ID NO 8
<211> LENGTH: 1437
<212> TYPE: DNA
<213> ORGANISM: Penicillium chrysogenum

<400> SEQUENCE: 8

| | | | | | |
|---|---|---|---|---|---|
| atgagcggcc | tacgcttcct | tgacttgatc | aagcccttta | cgcccctcct | cccggaggtg | 60 |
| gcagctcctg | agaccaaggt | gcccttcaac | cagaagttga | tgtggactgg | tttgactttg | 120 |

-continued

```
atgatcttcc tggtcatgag tcagatgcct ctttacggta ttgtctcctc cgacacttcg    180
gaccccctgt actggctccg tatgatgctg gccagtaacc ggggtactct gatggagctg    240
ggtatcaccc ctattatctc ctccggcatg gtcttccagc tccttgccgg tacccacctc    300
attgatgtca acctcgactt gaagaccgac cgcgagctct accagaccgc ccagaagctc    360
ttcgctatca ttctctcatt cggccaggcc tgtgtttacg tcctgactgg tctctacggc    420
cagcccagtg acctcggtgc cggtatctgt gttctcctga ttgtccagct cgttgtggcc    480
ggtctcgtcg tcattctgct tgacgagctc ctccagaagg ctacggtct  gggcagcggt    540
atctccctgt tcattgccac caacatttgc gagtccattg tctggaaggc tttctccccc    600
accaccatca acaccggccg tggccccgag ttcgagggtg ctatcatcgc tctgttccac    660
cttctcctga cctggcccga taagcagcgc gccctgtacg aggcgttcta ccgccagaac    720
ctgcccaacg tcatgaacct cctggctact cttctggtct cgccgctgt  catctacctg    780
cagggcttcc gtgttgagat ccccgtcaag tcctcccgcc agcgtggcat gcgcggctcg    840
taccccgtcc gcctcttcta cacctccaac atgcccatca tgctccagtc cgcgctgtgc    900
tccaacatct tcctcatcag tcagatgctg tactctcgct tctctgagaa catcctggtc    960
cagctccttg agtttggga gccccgtgag ggatctgctc agctttacgc cgcctctggt   1020
attgcttact acatgtcacc tcctctcaac ttcaaggagg ctcttctcga ccccatccac   1080
accgctgtct acattacctt catgcttgtt gcctgcgctc tcttctccaa gacctggatt   1140
gaggtttccg gctccgctcc ccgcgacgtt gctaagcagc tcaaggacca gggtcttgtc   1200
atgtctggtc accgtgagca gagcatgtac aaggagctga agcgcgttat ccctactgcc   1260
gctgctttcg gtggtgcctg cattggtggc ctgtccgtcg cctccgacct tatgggtgct   1320
ctcggcagtg gtactggtat tcttcttgcc gttaccatca tctacggcta ctttgaaatt   1380
gccgcccgtg agggtgacat tggcgctggc ctcaagggcc tcgtccccgg cagctaa     1437
```

<210> SEQ ID NO 9
<211> LENGTH: 478
<212> TYPE: PRT
<213> ORGANISM: Penicillium chrysogenum

<400> SEQUENCE: 9

```
Met Ser Gly Leu Arg Phe Leu Asp Leu Ile Lys Pro Phe Thr Pro Leu
 1               5                  10                  15

Leu Pro Glu Val Ala Ala Pro Glu Thr Lys Val Pro Phe Asn Gln Lys
            20                  25                  30

Leu Met Trp Thr Gly Leu Thr Leu Met Ile Phe Leu Val Met Ser Gln
        35                  40                  45

Met Pro Leu Tyr Gly Ile Val Ser Ser Asp Thr Ser Asp Pro Leu Tyr
    50                  55                  60

Trp Leu Arg Met Met Leu Ala Ser Asn Arg Gly Thr Leu Met Glu Leu
65                  70                  75                  80

Gly Ile Thr Pro Ile Ile Ser Ser Gly Met Val Phe Gln Leu Leu Ala
                85                  90                  95

Gly Thr His Leu Ile Asp Val Asn Leu Asp Leu Lys Thr Asp Arg Glu
            100                 105                 110

Leu Tyr Gln Thr Ala Gln Lys Leu Phe Ala Ile Ile Leu Ser Phe Gly
        115                 120                 125

Gln Ala Cys Val Tyr Val Leu Thr Gly Leu Tyr Gly Gln Pro Ser Asp
    130                 135                 140
```

```
Leu Gly Ala Gly Ile Cys Val Leu Leu Ile Val Gln Leu Val Val Ala
145                 150                 155                 160

Gly Leu Val Val Ile Leu Leu Asp Glu Leu Leu Gln Lys Gly Tyr Gly
                165                 170                 175

Leu Gly Ser Gly Ile Ser Leu Phe Ile Ala Thr Asn Ile Cys Glu Ser
            180                 185                 190

Ile Val Trp Lys Ala Phe Ser Pro Thr Thr Ile Asn Thr Gly Arg Gly
        195                 200                 205

Pro Glu Phe Glu Gly Ala Ile Ile Ala Leu Phe His Leu Leu Leu Thr
    210                 215                 220

Trp Pro Asp Lys Gln Arg Ala Leu Tyr Glu Ala Phe Tyr Arg Gln Asn
225                 230                 235                 240

Leu Pro Asn Val Met Asn Leu Leu Ala Thr Leu Leu Val Phe Ala Ala
                245                 250                 255

Val Ile Tyr Leu Gln Gly Phe Arg Val Glu Ile Pro Val Lys Ser Ser
            260                 265                 270

Arg Gln Arg Gly Met Arg Gly Ser Tyr Pro Val Arg Leu Phe Tyr Thr
        275                 280                 285

Ser Asn Met Pro Ile Met Leu Gln Ser Ala Leu Cys Ser Asn Ile Phe
    290                 295                 300

Leu Ile Ser Gln Met Leu Tyr Ser Arg Phe Ser Glu Asn Ile Leu Val
305                 310                 315                 320

Gln Leu Leu Gly Val Trp Glu Pro Arg Glu Gly Ser Ala Gln Leu Tyr
                325                 330                 335

Ala Ala Ser Gly Ile Ala Tyr Tyr Met Ser Pro Pro Leu Asn Phe Lys
            340                 345                 350

Glu Ala Leu Leu Asp Pro Ile His Thr Ala Val Tyr Ile Thr Phe Met
        355                 360                 365

Leu Val Ala Cys Ala Leu Phe Ser Lys Thr Trp Ile Glu Val Ser Gly
370                 375                 380

Ser Ala Pro Arg Asp Val Ala Lys Gln Leu Lys Asp Gln Gly Leu Val
385                 390                 395                 400

Met Ser Gly His Arg Glu Gln Ser Met Tyr Lys Glu Leu Lys Arg Val
                405                 410                 415

Ile Pro Thr Ala Ala Ala Phe Gly Gly Ala Cys Ile Gly Gly Leu Ser
            420                 425                 430

Val Ala Ser Asp Leu Met Gly Ala Leu Gly Ser Gly Thr Gly Ile Leu
        435                 440                 445

Leu Ala Val Thr Ile Ile Tyr Gly Tyr Phe Glu Ile Ala Ala Arg Glu
    450                 455                 460

Gly Asp Ile Gly Ala Gly Leu Lys Gly Leu Val Pro Gly Ser
465                 470                 475

<210> SEQ ID NO 10
<211> LENGTH: 38
<212> TYPE: DNA
<213> ORGANISM: Artificial Sequence
<220> FEATURE:
<223> OTHER INFORMATION: Synthetic primer

<400> SEQUENCE: 10
gtcctgttaa ttaaccacca tgagcggccg tgagttcc                            38

<210> SEQ ID NO 11
<211> LENGTH: 34
<212> TYPE: DNA
<213> ORGANISM: Artificial Sequence
```

```
<220> FEATURE:
<223> OTHER INFORMATION: Synthetic primer

<400> SEQUENCE: 11
acttcaggcg cgccttagct gccggggacg aggc                              34

<210> SEQ ID NO 12
<211> LENGTH: 38
<212> TYPE: DNA
<213> ORGANISM: Artificial Sequence
<220> FEATURE:
<223> OTHER INFORMATION: Synthetic primer

<400> SEQUENCE: 12
gtcctgttaa ttaaccacca tgagcggcct acgcttcc                          38

<210> SEQ ID NO 13
<211> LENGTH: 38
<212> TYPE: DNA
<213> ORGANISM: Artificial Sequence
<220> FEATURE:
<223> OTHER INFORMATION: Synthetic primer

<400> SEQUENCE: 13
gtcctgttaa ttaaccacca tgagcggacg tgagtctt                          38

<210> SEQ ID NO 14
<211> LENGTH: 34
<212> TYPE: DNA
<213> ORGANISM: Artificial Sequence
<220> FEATURE:
<223> OTHER INFORMATION: Synthetic primer

<400> SEQUENCE: 14
acttcaggcg cgccctagtt acccggaaca aggc                              34

<210> SEQ ID NO 15
<211> LENGTH: 37
<212> TYPE: DNA
<213> ORGANISM: Artificial Sequence
<220> FEATURE:
<223> OTHER INFORMATION: Synthetic primer

<400> SEQUENCE: 15
gtcctgttaa ttaaccacca tgagcggact ccggttt                           37

<210> SEQ ID NO 16
<211> LENGTH: 27
<212> TYPE: DNA
<213> ORGANISM: Artificial Sequence
<220> FEATURE:
<223> OTHER INFORMATION: Synthetic primer

<400> SEQUENCE: 16
gtgctctctt ctggaagacc tggattg                                      27

<210> SEQ ID NO 17
<211> LENGTH: 27
<212> TYPE: DNA
<213> ORGANISM: Artificial Sequence
<220> FEATURE:
<223> OTHER INFORMATION: Synthetic primer

<400> SEQUENCE: 17
caatccaggt cttccagaag agagcac                                      27
```

```
<210> SEQ ID NO 18
<211> LENGTH: 30
<212> TYPE: DNA
<213> ORGANISM: Artificial Sequence
<220> FEATURE:
<223> OTHER INFORMATION: Synthetic primer

<400> SEQUENCE: 18
taggcgcgcc atgagcggac gtgagtcttg                                    30

<210> SEQ ID NO 19
<211> LENGTH: 37
<212> TYPE: DNA
<213> ORGANISM: Artificial Sequence
<220> FEATURE:
<223> OTHER INFORMATION: Synthetic primer

<400> SEQUENCE: 19
tagcggccgc gaattcgaga tggtcaagcc aattaag                             37

<210> SEQ ID NO 20
<211> LENGTH: 21
<212> TYPE: DNA
<213> ORGANISM: Artificial Sequence
<220> FEATURE:
<223> OTHER INFORMATION: Synthetic primer

<400> SEQUENCE: 20
gtaatcctgc agctctggga g                                             21

<210> SEQ ID NO 21
<211> LENGTH: 18
<212> TYPE: DNA
<213> ORGANISM: Artificial Sequence
<220> FEATURE:
<223> OTHER INFORMATION: Synthetic primer

<400> SEQUENCE: 21
cctcaatcca ggtcttgg                                                 18

<210> SEQ ID NO 22
<211> LENGTH: 18
<212> TYPE: DNA
<213> ORGANISM: Artificial Sequence
<220> FEATURE:
<223> OTHER INFORMATION: Synthetic primer

<400> SEQUENCE: 22
cctcaatcca ggtcttcc                                                 18

<210> SEQ ID NO 23
<211> LENGTH: 7
<212> TYPE: PRT
<213> ORGANISM: Artificial Sequence
<220> FEATURE:
<223> OTHER INFORMATION: synthetic peptide

<400> SEQUENCE: 23

Ala Leu Phe Ser Lys Thr Trp
1               5
```

PRODUCTION OF POLYPEPTIDES BY IMPROVED SECRETION

This application is a U.S. national stage of International Patent Application No. PCT/EP2005/052805, filed 16 Jun. 2005, which designated the U.S. and claims priority of EP 04076775.8, filed 16 Jun. 2004; the entire contents of each of which are hereby incorporated by reference.

FIELD OF THE INVENTION

The present invention relates to recombinant-DNA technology. Specifically this invention relates to SEC61 polypeptides that have protein transport activity as described for yeast SEC61 (*Saccharomyces* Genome Database—SGD), nucleic acid sequences encoding these polypeptides and the use thereof in the preparation of host cells suitable for production of a polypeptide of interest.

BACKGROUND OF THE INVENTION

Secretion of the proteins into the culture medium involves transfer of the proteins through the various membrane-enclosed compartments constituting the secretory pathway. First the proteins are translocated into the lumen of the endoplasmic reticulum, ER. From there on the proteins are transported in membrane vesicles to the Golgi complex and from Golgi to plasma membrane. The secretory process involves several steps in which vesicles containing the secreted proteins are pinched off from the donor membrane, targeted to and fused with the acceptor membrane. At each of these steps functions of several different proteins are needed.

Several attempts have been made to increase protein secretion in filamentous fungi. A common approach to increase secretion of heterologous proteins is to use signal sequences (see for example EP 0215 594). Random mutagenesis and screening for a secreted protein (Smith et al., 1985; Sakai et al., 1988; Shuster et al., 1989; Suzuki et al., 1989; Sleep et al., 1991; Lamsa and Bloebaum, 1990; Dunn-Coleman et al., 1991 and US 2002/0068325 A1) or fusion of the foreign protein to an efficiently secreted endogenous protein (Ward et al., 1990; Harkki et al., 1989; Nyyssonen et al 1993; Nyyssönen et al., 1992) have been widely used both for yeast and filamentous fungi in order to make the secretion of heterologous proteins more efficient. Both of these methods are of limited use. Mutants isolated by random mutagenesis and screening are almost exclusively recessive and thus cannot be transferred into industrial strains, which are polyploids. Often the mutants obtained have only improved secretion capacities for the protein used for screening. Fusion protein approach requires tailoring of the fusion construction for each heterologous or foreign protein separately. The fusion protein is often not functional and thus the final product must be released by proteolytic cleavage, which complicates the production procedure.

Due to their industrial importance as protein producer, there is still a need to obtain filamentous fungi with improved secretion capacity.

DETAILED DESCRIPTION OF THE INVENTION

Figure 1:
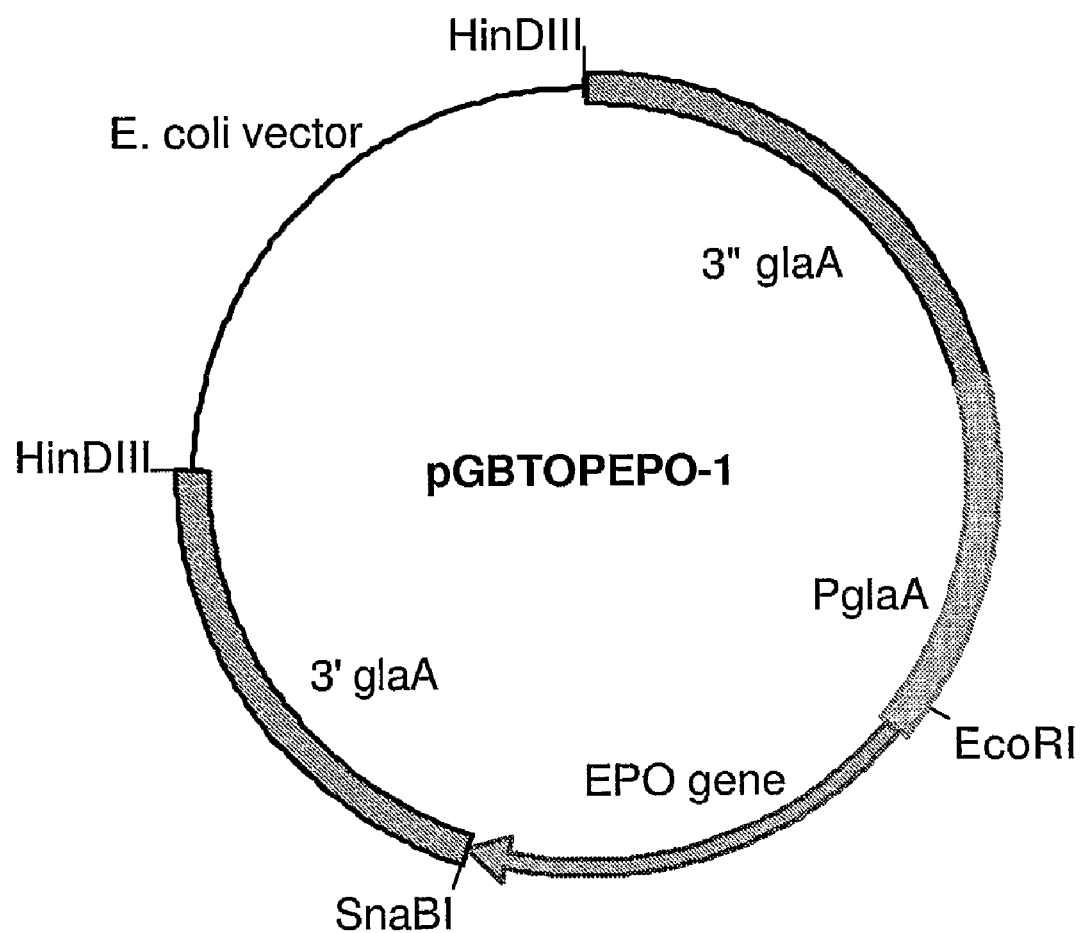
FIG. 1: Plasmid map of the proline specific endoprotease expression vector pGBTOPEPO-1. Indicated are the glaA flanking regions relative to the glaA promoter and the proline specific endoprotease epo gene. The *E. coli* DNA can be removed by digestion with restriction enzyme HinDIII, prior to transformation to the *A. niger* strains.

All patents and publications, including all sequences and methods disclosed within such patents and publications, referred to herein are expressly incorporated by reference. These patents and publications include: EP 357 127, EP 635 574, WO 97/06261, WO 98/46772.

Polypeptides Displaying SEC61 Activity

A first aspect of the present invention relates to novel SEC61 polypeptides. SEC61 polypeptides are commonly known to mediate transport of a polypeptide across the ER membrane. A SEC61 polypeptide according to the invention is defined as a polypeptide that displays at least one activity commonly known to be associated with SEC61 polypeptides.

A SEC61 polypeptide according to the invention may also display all activities commonly known to be associated with SEC61 polypeptides.

Specifically, the present invention discloses a SEC61 polypeptide selected from the group consisting of:
  (a) a polypeptide having an amino acid sequence according to SEQ ID NO: 3, and
  (b) a polypeptide having an amino acid sequence that is substantially homologous to the amino acid sequence according to SEQ ID NO: 3.

In the context of the present invention, the term "substantially homologous" is meant to encompass polypeptides that display at least one activity of the SEC61 polypeptide and that have a degree of identity to the amino acid sequence set forth in SEQ ID NO: 3 of at least 89%, preferably at least 90%, even more preferably at least 92%, even more preferably at least 93%, even more preferably at least 94%, even more preferably at least 95%, even more preferably at least 96%, even more preferably at least 97%, even more preferably at least 98% and most preferably at least 99%. The degree of identity preferably is measured over the whole length of SEQ ID NO: 3.

For the purpose of the present invention, the degree of identity between two amino acid sequences refers to the percentage of amino acids that are identical between the two sequences. The degree of identity is determined using the BLAST algorithm, which is described in Altschul, et al., J. Mol. Biol. 215: 403-410 (1990). Software for performing BLAST analyses is publicly available through the National Center for Biotechnology Information. The BLAST algorithm parameters W, T, and X determine the sensitivity and speed of the alignment. The BLAST program uses as defaults a word length (W) of 11, the BLOSUM62 scoring matrix (see Henikoff & Henikoff, Proc. Natl. Acad. Sci. USA 89: 10915 (1989)) alignments (B) of 50, expectation (E) of 10, M=5, N=−4, and a comparison of both strands.

In a preferred embodiment, the polypeptide of the invention has an amino acid sequence according to SEQ ID NO: 3.

In another embodiment, the amino acid sequence of the polypeptide that is substantially homologous to the amino acid sequence according to SEQ ID NO: 3 may differ in amino acid sequence with SEQ ID NO: 3 due to natural or artificial variation (mutagenesis). The polypeptide having an amino acid sequence that is substantially homologous to the amino acid sequence according to SEQ ID NO: 3 may contain at least one modification as compared to the sequence of SEQ ID NO: 3. Said modification may be an amino acid substitution, addition or deletion.

In a preferred embodiment, the polypeptide of the invention has an amino acid sequence which differs by five amino acids, preferably by four amino acids, more preferably by three amino acids, even more preferably by two amino acids, and most preferably by one amino acid from the amino acid sequence set forth in SEQ ID NO: 3 and still has the same SEC61 activity as the polypeptide having the amino acid sequence set forth in SEQ ID NO: 3.

In another preferred embodiment, a polypeptide having an amino acid sequence that is substantially homologous to the amino acid sequence according to SEQ ID NO: 3 has an amino acid sequence according to SEQ ID NO: 9.

In another preferred embodiment of the invention, a SEC61 polypeptide is provided that has a degree of identity to the amino acid sequence according to SEQ ID NO: 3 of at least 85%, preferably at least 87%, more preferably at least 89%, even more preferably at least 90%, even more preferably at least 92%, even more preferably at least 93%, even more preferably at least 94%, even more preferably at least 95%, even more preferably at least 96%, even more preferably at least 97%, even more preferably at least 98% and most preferably at least 99%, wherein at least one amino acid is modified in a consensus motif corresponding to position 373 to 379 of SEQ ID NO: 3, i.e. corresponding to the amino acid sequence ALFSKTW (SEQ ID NO: 23) present at position 373 to 379 of SEQ ID NO: 3. Preferably, the at least one amino acid that is modified in the consensus motif is at a position corresponding to position 376 of SEQ ID NO: 3. More preferably, the amino acid at a position corresponding to position 376 of SEQ ID NO: 3 is replaced by tryptophan, phenylalanine, tyrosine or histidine. Most preferably, serine at a position corresponding to position 376 of SEQ ID NO: 3 is replaced by tryptophan. An example of such a modified SEC61 polypeptide is a polypeptide having an amino acid sequence according to SEQ ID NO: 6.

Further variations in the consensus motif may be the presence of leucine, valine, phenylalanine or methinone at a position corresponding to position 374 of SEQ ID NO: 3, and/or the presence of lysine, alanine, threonine or arginine at a position corresponding to position 377 of SEQ ID NO: 3, and/or the presence of threonine or leucine at a position corresponding to position 378 of SEQ ID NO: 3.

Isolated Filamentous Fungal Nucleic Acid Sequences Encoding a SEC61 Polypeptide

A second aspect of the present invention relates to an isolated polynucleotide comprising a nucleic acid sequence encoding a SEC61 polypeptide of the first aspect.

In particular, the polynucleotide or nucleic acid sequence encoding a SEC61 polypeptide is selected from the group consisting of:
  (a) the polynucleotide according to SEQ ID NO: 1,
  (b) the nucleic acid sequence according to SEQ ID NO: 2,
  (c) a nucleic acid sequence having a degree of identity of at least 90% to the nucleic acid sequence of SEQ ID NO: 2, and
  (d) a nucleic acid sequence encoding a polypeptide having an amino acid sequence that is substantially homologous to the amino acid sequence of SEQ ID NO: 3.

In a preferred embodiment, the nucleic acid sequence of feature (c) has a degree of identity to the nucleic acid sequence set forth in SEQ ID NO: 2 of at least 91%, more preferably at least 92%, even more preferably at least 93%, even more preferably at least 94%, even more preferably at least 95%, even more preferably at least 96%, even more preferably at least 97%, even more preferably at least 98%, most preferably at least 99%.

For purposes of the present invention, the degree of identity between two nucleic acid sequences is determined by the Clustal method (Higgins, 1989, CABIOS 5: 151-153) with an identity table, a gap penalty of 10, and a gap length penalty of 10.

In another preferred embodiment, the isolated nucleic acid sequence encodes a polypeptide having the amino acid sequence of SEQ ID NO: 3, or a fragment thereof having SEC61 activity.

In another preferred embodiment, the isolated nucleic acid sequence encodes a polypeptide having the amino acid sequence of SEQ ID NO: 9, or a fragment thereof having SEC61 activity.

In another preferred embodiment, the nucleic acid sequence encoding a SEC61 polypeptide has a nucleic acid sequence as set forth in SEQ ID NO: 2 or in SEQ ID NO: 8.

In another preferred embodiment, the isolated nucleic acid sequence encodes a SEC61 polypeptide having an amino acid sequence that has a degree of identity to the amino acid sequence according to SEQ ID NO: 3 of at least 85%, wherein at least one amino acid is modified in the consensus motif corresponding to position 373 to 379 of SEQ ID NO: 3, i.e. corresponding to the amino acid sequence ALFSKTW (SEQ ID NO: 23) present at position 373 to 379 of SEQ ID NO: 3. For instance, the isolated nucleic acid sequence encodes a polypeptide having an amino acid sequence according to SEQ ID NO: 6, preferably is the nucleic acid sequence of SEQ ID NO: 5.

The term "isolated polynucleotide or nucleic acid sequence" as used herein refers to a polynucleotide or nucleic acid sequence which is essentially free of other nucleic acid sequences, e.g., at least about 20% pure, preferably at least about 40% pure, more preferably at least about 60% pure, even more preferably at least about 80% pure, most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced.

The polynucleotide or nucleic acid sequence may be of genomic, cDNA, RNA, semi-synthetic, synthetic origin, or any combinations thereof.

An isolated nucleic acid molecule encoding a SEC61 polypeptide and having an amino acid sequence that is substantially homologous to the protein according to SEQ ID NO: 3 may contain one or more nucleotide modifications, i.e. substitutions, additions or deletions, as compared to the coding nucleotide sequence according to SEQ ID NO: 2, such that one or more amino acid modifications, i.e. substitutions, deletions or insertions, are present in the encoded protein. Such modifications may be due to natural variation or may be introduced by standard mutagenesis techniques, such as site-directed mutagenesis or PCR-mediated mutagenesis.

It is also possible to introduce nucleotide substitutions into a sec61 coding sequence that do not give rise to a different amino acid residue in the polypeptide encoded by the nucleic acid sequence. This may for instance be advantageous to create a nucleic acid sequence wherein the codon use corresponds to the codon use of the host organism intended for expression of the SEC61 protein.

It will be apparent for the person skilled in the art that DNA sequence polymorphisms that may lead to changes in the amino acid sequence of the encoded protein may naturally exist within a given population. Such genetic polymorphisms may exist in cells from different populations or within a population due to natural allelic variation.

The SEC61 polypeptides according to the invention and the encoding nucleic acid sequences may be obtained from any eukaryotic cell, preferably from a fungus, more preferably from a filamentous fungus.

"Filamentous fungi" include all filamentous forms of the subdivision Eumycota and Oomycota (as defined by Hawksworth et al., 1995, supra). Filamentous fungal strains include, but are not limited to, strains of *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium,* and *Trichoderma*.

In a more preferred embodiment, the nucleic acid sequence encoding a polypeptide having SEC61 activity of the present invention is obtained from a strain of *Aspergillus*, such as *A. awamori* or *A. nidulans*. Preferably, the nucleic acid sequence is obtained from a strain of *A. niger* or *A. oryzae*. Even more preferably, the nucleic acid sequence is obtained from an isolate of a strain of *A. niger*, e.g. the nucleic acid sequence set forth in SEQ ID NO: 1 or in SEQ ID NO: 2.

In another embodiment, the nucleic acid sequence encoding a polypeptide having SEC61 activity of the present invention is obtained from a strain of *Fusarium*, such as *F. oxysporum* or *F. venenatum*, or a strain of *Penicillium*, such as *P. chrysogenum*., e.g. the nucleic acid sequence set forth in SEQ ID NO: 7 or in SEQ ID NO: 8.

It will be understood that for the aforementioned species, the invention encompasses both the perfect and imperfect states, and other taxonomic equivalents, e.g. anamorphs, regardless of the species name by which they are known. Those skilled in the art will readily recognize the identity of appropriate equivalents. For example, the polypeptides may be obtained from micro-organisms, which are taxonomic equivalents of *Aspergillus* as defined by Raper, K. D. and Fennel, D. I. (1965. The Genus *Aspergillus*, The Wilkins Company, Baltimore Md.), regardless of the species name by which they are known.

Furthermore, polypeptides having SEC61 activity may be identified and obtained from other sources than filamentous fungi, including micro-organisms isolated from nature (e.g., soil, composts, water, etc.) using e.g. probes based on the polynucleotides according to the present invention. Techniques for isolating micro-organisms from natural habitats are well known in the art.

DNA sequences encoding SEC61 polypeptides of the invention may be obtained by hybridisation. Nucleic acid molecules corresponding to variants (e.g. natural allelic variants) and homologues of the sec61 DNA of the invention can be isolated based on their homology to the nucleic acids disclosed herein using these nucleic acids or a suitable fragment thereof, as a hybridisation probe according to standard hybridisation techniques, preferably under highly stringent hybridisation conditions.

"Stringency" of hybridization reactions is readily determinable by one of ordinary skill in the art. For additional details and explanation of stringency of hybridization reactions, see Ausubel et al, Current Protocols in Molecular Biology, Wiley Interscience Publishers, (1995).

The nucleic acid sequence may be isolated by e.g. screening a genomic or cDNA library of the micro-organism in question. Once a nucleic acid sequence encoding a polypeptide having SEC61 activity has been detected with e.g a probe derived form SEQ ID NO: 2, the sequence may be isolated or cloned by utilizing techniques which are known to those of ordinary skill in the art (see, e.g., J. Sambrook, E. F. Fritsch, and T. Maniatis, 1989, Molecular Cloning, A Laboratory Manual, 2d edition, Cold Spring Harbor, N.Y.).

The cloning of the nucleic acid sequences of the present invention from such genomic DNA can also be effected, e.g. by using methods based on polymerase chain reaction (PCR) or antibody screening of expression libraries to detect cloned DNA fragments with shared structural features (See, e.g., Innis et al., 1990, PCR: A Guide to Methods and Application, Academic Press, New York.).

The sequence information as provided herein should not be so narrowly construed as to require inclusion of erroneously identified bases. The specific sequences disclosed herein can be readily used to isolate the complete gene from filamentous fungi, in particular *A. niger*, which in turn can easily be subjected to further sequence analyses thereby identifying sequencing errors.

Unless otherwise indicated, all nucleotide sequences determined by sequencing a DNA molecule herein were determined using an automated DNA sequencer and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

The person skilled in the art is capable of identifying such erroneously identified bases and knows how to correct for such errors.

Nucleic Acid Constructs

Another aspect of the present invention relates to nucleic acid constructs comprising a nucleic acid sequence encoding the SEC61 polypeptide according to the invention, operably linked to one or more control sequences, which direct the expression of the polypeptide having SEC61 activity in a suitable expression host.

Expression will be understood to include any step involved in the production of the polypeptide and may include transcription, post-transcriptional modification, translation, post-translational modification, secretion.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression vector or cassette when the nucleic acid construct contains all the control sequences required for expression of a coding sequence in a particular host organism.

The term "control sequences" is defined herein to include all components, which are necessary or advantageous for the expression of a polypeptide. Each control sequence may be native or foreign to the nucleic acid sequence encoding the polypeptide. Such control sequences may include, but are not limited to, a promoter, a leader, optimal translation initiation sequences (as described in Kozak, 1991, J. Biol. Chem. 266: 19867-19870), a secretion signal sequence, a pro-peptide sequence, a polyadenylation sequence, a transcription terminator. At a minimum, the control sequences include a promoter, and transcriptional and translational stop signals.

The term "operably linked" is defined herein as a configuration in which a control sequence is appropriately placed at a position relative to the coding sequence of the DNA sequence such that the control sequence directs the production of a polypeptide.

The control sequence may be an appropriate promoter sequence containing transcriptional control sequences. The promoter may be any nucleic acid sequence, which shows transcription regulatory activity in the cell including mutant, truncated, and hybrid promoters, and may be obtained from genes encoding extracellular or intracellular polypeptides. The promoter may be either homologous or heterologous to the cell or to the polypeptide.

Preferred promoters for filamentous fungal cells are known in the art and can be, for example, the glucose-6-phosphate dehyrogenase gpdA promoters, protease promoters such as pepA, pepB, pepC, the glucoamylase glaA promoters, amylase amyA, amyB promoters, the catalase catR or catA promoters, glucose oxidase goxC promoter, beta-galactosidase lacA promoter, alpha-glucosidase aglA promoter, translation elongation factor tefA promoter, xylanase promoters such as xlnA, xlnB, xlnC, xlnD, cellulase promoters such as eglA, eglB, cbhA, promoters of transcriptional regulators such as areA, creA, xlnR, pacC, prtT, etc or any other, and can be found among others at the NCBI website.

In a preferred embodiment, the promoter may be derived from a gene, which is highly expressed (defined herein as the mRNA concentration with at least 0.5% (w/w) of the total cellular mRNA). In another preferred embodiment, the promoter may be derived from a gene, which is medium expressed (defined herein as the mRNA concentration with at least 0.01% until 0.5% (w/w) of the total cellular mRNA). In another preferred embodiment, the promoter may be derived from a gene, which is low expressed (defined herein as the mRNA concentration lower than 0.01% (w/w) of the total cellular mRNA).

The control sequence may also be a suitable transcription terminator sequence, a sequence recognized by a filamentous fungal cell to terminate transcription. The terminator sequence is operably linked to the 3' terminus of the nucleic acid sequence encoding the polypeptide. Any terminator, which is functional in the cell, may be used in the present invention.

Preferred terminators for filamentous fungal cells are obtained from the genes encoding A. oryzae TAKA amylase, A. niger glucoamylase, A. nidulans anthranilate synthase, A. niger alpha-glucosidase, trpC gene and Fusarium oxysporum trypsin-like protease.

The control sequence may also be a suitable leader sequence, a non-translated region of a mRNA which is important for translation by the filamentous fungal cell. The leader sequence is operably linked to the 5' terminus of the nucleic acid sequence encoding the polypeptide. Any leader sequence, which is functional in the cell, may be used in the present invention.

Preferred leaders for filamentous fungal cells are obtained from the genes encoding A. oryzae TAKA amylase and A. nidulans triose phosphate isomerase and A. niger glaA.

The control sequence may also be a polyadenylation sequence, a sequence which is operably linked to the 3' terminus of the nucleic acid sequence and which, when transcribed, is recognized by the filamentous fungal cell as a signal to add polyadenosine residues to transcribed mRNA. Any polyadenylation sequence, which is functional in the cell, may be used in the present invention.

Preferred polyadenylation sequences for filamentous fungal cells are obtained from the genes encoding A. oryzae TAKA amylase, A. niger glucoamylase, A. nidulans anthranilate synthase, Fusarium oxyporum trypsin-like protease and A. niger alpha-glucosidase.

For a polypeptide to be secreted, the control sequence may also be a signal peptide-encoding region, which codes for an amino acid sequence linked to the amino terminus of the polypeptide, which can direct the encoded polypeptide into the cell's secretory pathway. The 5'end of the coding sequence of the nucleic acid sequence may inherently contain a signal peptide-coding region naturally linked in translation reading frame with the segment of the coding region, which encodes the secreted polypeptide. Alternatively, the 5'end of the coding sequence may contain a signal peptide-coding region, which is foreign to the coding sequence. The foreign signal peptide-coding region may be required where the coding sequence does not normally contain a signal peptide-coding region. Alternatively, the foreign signal peptide-coding region may simply replace the natural signal peptide-coding region in order to obtain enhanced secretion of the polypeptide.

The nucleic acid construct may be an expression vector. The expression vector may be any vector (e.g. a plasmid or virus), which can be conveniently subjected to recombinant DNA procedures and can bring about the expression of the nucleic acid sequence encoding the polypeptide. The choice of the vector will typically depend on the compatibility of the vector with the cell into which the vector is to be introduced. The vectors may be linear or closed circular plasmids.

The vector may be an autonomously replicating vector, i.e. a vector, which exists as an extrachromosomal entity, the replication of which is independent of chromosomal replication, e.g. a plasmid, an extrachromosomal element, a minichromosome, or an artificial chromosome. An autonomously maintained cloning vector for a filamentous fungus may comprise the AMA1-sequence (see e.g. Aleksenko and Clutterbuck (1997), Fungal Genet. Biol. 21: 373-397).

Alternatively, the vector may be one which, when introduced into the cell, is integrated into the genome and replicated together with the chromosome(s) into which it has been integrated. The integrative cloning vector may integrate at random or at a predetermined target locus in the chromosomes of the host cell. In a preferred embodiment of the invention, the integrative cloning vector comprises a DNA fragment, which is homologous to a DNA sequence in a predetermined target locus in the genome of host cell for targeting the integration of the cloning vector to this predetermined locus. In order to promote targeted integration, the cloning vector is preferably linearized prior to transformation of the host cell. Linearization is preferably performed such that at least one but preferably either end of the cloning vector is flanked by sequences homologous to the target locus. The length of the homologous sequences flanking the target locus is preferably at least at least 0.1 kb, even preferably at least 0.2 kb, more preferably at least 0.5 kb, even more preferably at least 1 kb, most preferably at least 2 kb.

According to a preferred embodiment, the target locus of integration of the expression vector comprising a gene encoding the SEC61 polypeptide according to the invention is the sec61 locus.

The vector system may be a single vector or plasmid or two or more vectors or plasmids, which together contain the total DNA to be introduced into the genome of the host cell, or a transposon.

The vectors preferably contain one or more selectable markers, which permit easy selection of transformed cells. A selectable marker is a gene the product of which provides for biocide or viral resistance, resistance to heavy metals, prototrophy to auxotrophs, and the like. A selectable marker for use in a filamentous fungal cell may be selected from the group including, but not limited to, amdS (acetamidase), argB (ornithine carbamoyltransferase), bar (phosphinothricinacetyltransferase), hygB (hygromycinphosphotransferase), niaD (nitrate reductase), pyrG (orotidine-5'-phosphate decarboxylase), sC (sulfate adenyltransferase), and trpC (anthranilate synthase), as well as equivalents from other species. Preferred for use in an *Aspergillus* cell are the amdS (EP 635574B1, WO 97/06261) and pyrG genes of *A. nidulans* or *A. oryzae* and the bar gene of *Streptomyces hygroscopicus*. More preferably an amdS gene is used, even more preferably an amdS gene from *A. nidulans* or *A. niger*. A most preferred selection marker gene is the *A. nidulans* amdS coding sequence fused to the *A. nidulans* gpdA promoter (see EP 635 574). AmdS genes from other filamentous fungus may also be used (WO 97/06261).

Host Cells

In another aspect, the present invention provides host cells suitable for the production of a polypeptide of interest, said host cells over-expressing the polypeptide according to the invention having SEC61 activity. Said host cells comprise a nucleic acid construct or an expression vector encoding a SEC61 polypeptide according to the present invention.

Surprisingly, we found that fungal cells, in particular filamentous fungal cells, wherein a SEC61 polypeptide according to the invention, in particular a mutant SEC61 polypeptide modified in the consensus motif as described above, is over-expressed have improved protein secretion capacities as compared to fungal cells that do not over-express such a SEC61 polypeptide. Especially, the secretion of heterologous protein is improved. Optionally, the endogenous sec61 gene may be inactivated in cells over-expressing a SEC61 polypeptide that is modified as compared to the endogenous SEC61 polypeptide.

In a preferred embodiment, a host cell over-expressing a SEC61 polypeptide according to the invention expresses an amount of SEC61 polypeptide according to the invention that is at least 50% more than the amount of endogenously expressed SEC61 polypeptide, preferably at least 100% more, more preferably at least 200% more, most preferably at least 400% more. The amount of endogenously expressed SEC61 polypeptide is the amount of SEC61 polypeptide that is expressed by the parental host cell from which the host cell that over-expresses SEC61 polypeptide according to the invention is derived. The amount of expressed SEC61 polypeptide may be measured by any method known to the skilled person, for instance by quantitative SDS-PAGE, two-dimensional protein electrophoresis or Western blotting.

The present invention contemplates various embodiments of a host cell over-expressing a SEC61 polypeptide according to the invention.

In one embodiment, a host cell is provided that over-expresses a native SEC61 polypeptide, whereby the native SEC61 polypeptide is the same polypeptide as the SEC61 polypeptide naturally produced by said host.

In another embodiment, a host cell is provided that expresses a SEC61 polypeptide not naturally produced by said host. Optionally, such a host cell does not express the native SEC61 polypeptide. Not expressing the native SEC61 polypeptide may be accomplished by e.g. inactivating the endogenous sec61 gene. Preferably, inactivation of the endogenous sec61 gene may be accomplished by gene replacement, for instance as described in EP 0 357 127. More preferably, said gene replacement comprises a replacement of the endogenous sec61 gene by a nucleic acid construct (expression vector) comprising a nucleic acid sequence encoding the SEC61 polypeptide according to the invention.

The choice of a host cell in the methods of the present invention will to a large extent depend upon the source of the nucleic acid sequence encoding the polypeptide of interest. Preferably, the host cell is a eukaryotic cell, more preferably a fungus, most preferably a filamentous fungus. In a preferred embodiment, the filamentous fungal host cell is a cell of a species cited as species from which the SEC61 polypeptide according to the invention may be obtained.

In a preferred embodiment, a filamentous fungal host cell over-expresses a gene having a nucleic acid sequence encoding a polypeptide having an amino acid sequence which has at least 89% identity with the amino acid sequence of SEQ ID NO: 3, preferably a polypeptide with an amino acid sequence of SEQ ID NO: 3 or SEQ ID NO: 6 or SEQ ID NO: 9.

The obtained host cell may be used for producing a polypeptide of interest.

Thus, in another preferred embodiment, the host cell additionally harbours at least one copy of a polynucleotide comprising a nucleic acid sequence encoding a polypeptide of interest. The nucleic acid sequence may be cloned into an expression vector as described earlier for the expression of the sec61 gene. It will be understood that the methods of the present invention are not limited to a particular order for obtaining a filamentous fungal cell producing a polypeptide of interest. The introduction of the sec61 gene, optionally combined with the modification of the endogenous sec61 gene, may be done at any step in the construction of a cell for the production of a polypeptide of interest.

Producing a Polypeptide

Another aspect of the present invention relates to a method for the production of a polypeptide of interest in a host cell of the previous aspect, preferably a filamentous fungal host cell, comprising:
 (a) cultivating the host cell of the previous aspect in a nutrient medium suitable for production of the polypeptide of interest; and
 (b) recovering the polypeptide of interest from the nutrient broth.

The host cells of the present invention are cultivated in a nutrient medium suitable for production of the polypeptide of interest using methods known in the art. For example, the cells may be cultivated by shake flask cultivation, small-scale or large-scale fermentation (including continuous, batch, fed-batch, or solid state fermentations) in laboratory or industrial fermentors, performed in a suitable medium and under conditions allowing the polypeptide of interest to be expressed and/or isolated. The cultivation takes place in a suitable nutrient medium comprising at least carbon and nitrogen sources and inorganic salts, using procedures known in the art. The polypeptide of interest may be recovered from the nutrient medium by methods known in the art. If the polypeptide is secreted into the nutrient medium, the polypeptide may be recovered directly from the medium. If the polypeptide is not secreted, it may be recovered from cell lysates. If desired, the recovery may comprise further isolation and purification by conventional means.

For example, the polypeptide may be isolated by conventional procedures including, but not limited to, centrifugation, filtration, extraction, spray drying, evaporation, or precipitation. The isolated polypeptide may then be further purified by a variety of procedures known in the art including, but not limited to, chromatography (e.g. ion exchange, affinity, hydrophobic, chromatofocusing, and size exclusion), electrophoretic procedures (e.g., preparative isoelectric focusing), differential solubility (e.g., ammonium sulfate precipitation), or extraction (see, e.g., Protein Purification, J.-C. Janson and Lars Ryden, editors, VCH Publishers, New York, 1989).

Conveniently, the polypeptide of interest may be combined with suitable (solid or liquid) carriers or diluents including buffers to produce a polypeptide composition. The polypeptide may be attached to or mixed with a carrier, e.g. immobilized on a solid carrier.

The polypeptide of interest may be detected using methods known in the art that are specific for the polypeptide. These detection methods may include use of specific antibodies, formation of an enzyme product, disappearance of an enzyme substrate, or SDS PAGE. For example, an enzyme assay may be used to determine the activity of the polypeptide. Procedures for determining enzyme activity are known in the art for many enzymes.

In the methods of the present invention, the host cell, preferably the filamentous fungal host cell, produces at least about 20%, preferably at least about 50%, more preferably at least about 100%, even more preferably at least about 200%, and most preferably at least about 300% more of the polypeptide of interest than its corresponding counterpart cell not modified according to the invention with respect to SEC61 expression, when cultivated under identical conditions.

The polypeptide of interest may be a polypeptide homologous (native) or heterologous to the host cell. The term "polypeptide" is not meant herein to refer to a specific length of the encoded product and therefore encompasses peptides, oligopeptides and proteins.

A heterologous polypeptide may encompass a polypeptide, which is not naturally produced by the host cell. The polypeptide of interest may also encompass a polypeptide native to the host cell, which is encoded by a nucleic acid sequence, which expression is controlled by one or more control sequences foreign to the nucleic acid sequence encoding the polypeptide.

It is also possible to achieve over-expression of a SEC61 polypeptide of the invention in a strain that is not genetically modified to produce a polypeptide of interest, but that naturally produces such a polypeptide.

In a preferred embodiment, the polypeptide of interest is an antibody or a portion thereof, an antigen, a clotting factor, an enzyme, a hormone or a hormone variant, a receptor or a portion thereof, a regulatory protein, a structural protein, a reporter, or a transport protein.

In a more preferred embodiment, the polypeptide of interest is an enzyme, most preferably the enzyme is an oxidoreductase, transferase, hydrolase, lyase, isomerase, or ligase.

In an even more preferred embodiment, the enzyme is an aminopeptidase, amylase, carbohydrase, carboxypeptidase, catalase, cellulase, chitinase, cutinase, deoxyribonuclease, dextranase, esterase, alpha-galactosidase, beta-galactosidase, glucoamylase, amylase, alpha-glucosidase, beta-glucosidase, haloperoxidase, invertase, laccase, lipase, phospholipase, mannosidase, mutanase, oxidase, pectinase, peroxidase, phytase, polyphenoloxidase, protease, peptidase, ribonuclease, transglutaminase, or xylanase.

In another even more preferred embodiment, the polypeptide is human insulin or an analogue thereof, human growth hormone, erythropoietin, or insulinotropin.

The nucleic acid sequence encoding a polypeptide of interest may be obtained from any prokaryotic, eukaryotic, or other source. For purposes of the present invention, the term "obtained from" as used herein in connection with a given source shall mean that the polypeptide is produced by the source or by a cell in which a gene from the source has been inserted.

The present invention is further described by the following examples, which should not be construed as limiting the scope of the invention.

EXAMPLES

Experimental Information

Strains

WT 1: This *A. niger* strain is used as a wild-type strain. This strain is deposited at the CBS Institute under the deposit number CBS 513.88.

WT 2: This *A. niger* strain is a WT 1 strain comprising a deletion of the gene encoding glucoamylase (glaA). WT 2 is constructed by using the "MARKER-GENE FREE" approach as described in EP 0 635 574, wherein it is described how to delete glaA specific DNA sequences in the genome of CBS 513.88. The procedure results in a MARKER-GENE FREE ΔglaA recombinant *A. niger* CBS513.88 strain, possessing no foreign DNA sequences.

WT 3: This *A. niger* strain is a WT 2 strain comprising a deletion of the pepA gene encoding the major extracellular aspartic protease PepA. WT 3 is constructed by using the "MARKER-GENE FREE" approach as described in EP 0 635 574. The method described in this patent is used to delete pepA specific DNA sequences in the genome of CBS 513.88, as described by van den Hombergh et al. (van den Hombergh J P, Sollewijn Gelpke M D, van de Vondervoort P J, Buxton F P, Visser J. (1997)—Disruption of three acid proteases in *Aspergillus niger*—effects on protease spectrum, intracellular proteolysis, and degradation of target proteins—Eur J Biochem. 247(2): 605-13). The procedure results in a MARKER-GENE FREE ΔpepA, ΔglaA recombinant *A. niger* CBS513.88 strain, possessing no foreign DNA sequences.

WT 4: This *Penicillium chrysogenum* strain is used as a wild-type strain. This strain is deposited at the CBS Institute under the deposit number CBS 455.95.

EPO 1: This *A. niger* strain is a WT 2 strain comprising multiple copies of the *A. niger* epo gene coding for the proline specific endoprotease, which has been published elsewhere (WO 02/45524). EPO 1 is constructed by co-transformation of an amdS selectable marker-gene containing vector, which is designated pGBAAS-1 (constructed as described in EP 635 574) and the pGBTOPEPO-1 vector (FIG. 1) comprising the gene coding for the proline specific endoprotease as described in WO98/46772 and WO99/32617. The transformation and counterselection procedure results in a MARKER-GENE FREE EPO 1 strain containing multiple copies of the proline specific endoprotease encoding gene under control of the glucoamylase promoter.

Figure 2:
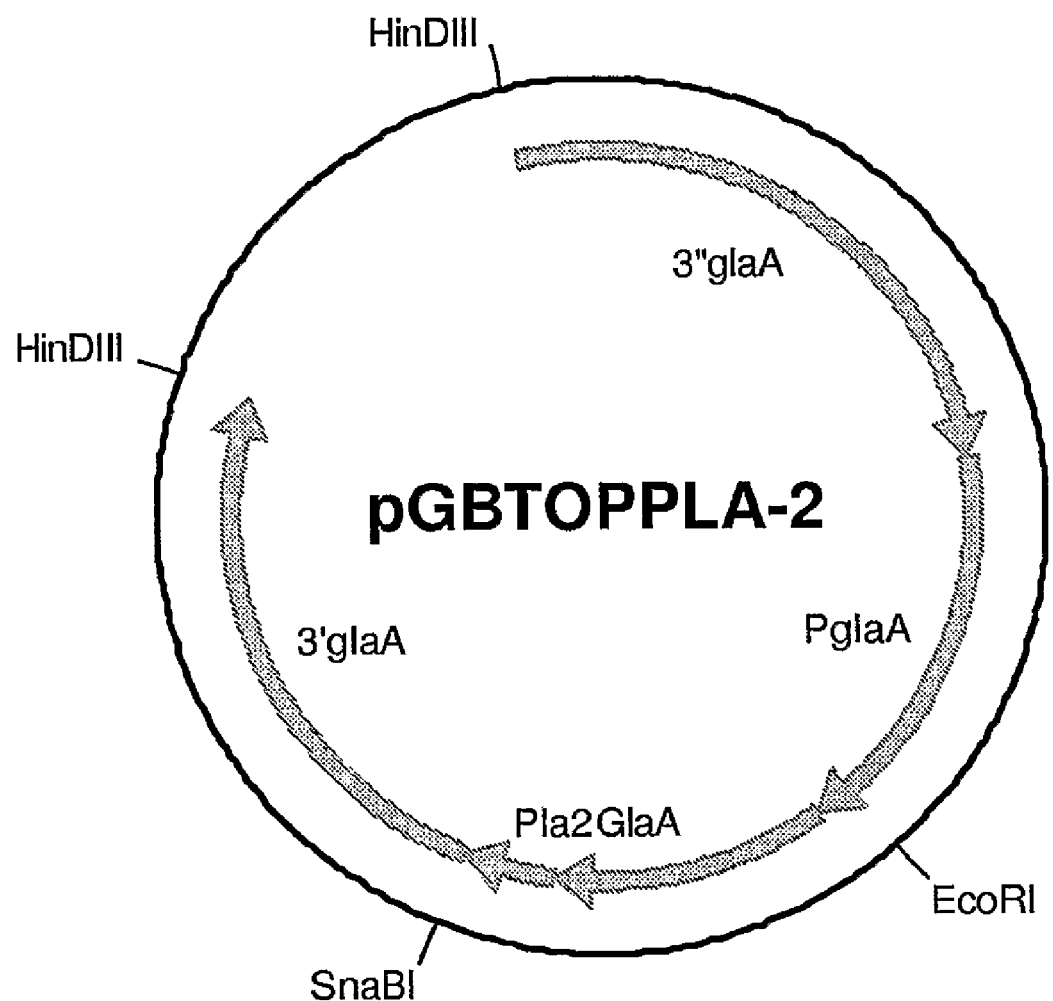
FIG. 2: Plasmid map of the PLA2 expression vector pGBTOPPLA-2. Indicated are the glaA flanking regions relative to the glaA promoter, the truncated glaA gene and the propla2 coding sequence. The *E. coli* DNA can be removed by digestion with restriction enzyme NotI, prior to transformation to the *A. niger* strains.

PLA 1: The heterologous porcine phospholipase A2 (PLA2) protein is selected as a model protein. It has been shown earlier that this protein is difficult to produce in *A. niger* in high quantities (Roberts I. N., Jeenes D. J., MacKenzie D. A., Wilkinson A. P., Sumner I. G. and Archer D. B. (1992)—Heterologous gene expression in *Aspergillus niger* a glucoamylase-porcine pancreatic phospholipase $A_2$ fusion protein is secreted and processed to yield mature enzyme. Gene 122: 155-161). The fragment for overexpression of PLA2 is made as a fusion of proPLA2 with a native glucoamylase A gene of *A. niger* and is prepared as described by Roberts et al. (1992). The fusion protein contains a kex1 splicing site in order to be processed in the Golgi. This glaA-pla2 fusion gene is cloned into an *A. niger* pGBTOP expression vector using the same techniques as described in WO 98/46772 and WO 99/32617, resulting in pGBTOPPLA-1 (FIG. 2).

The PLA 1 *A. niger* strain is a WT 3 strain comprising multiple copies of the glucoamylase-porcine pancreatic phospholipase $A_2$ fusion protein encoding gene. PLA 1 is constructed by co-transformation of the amdS selectable marker-gene containing vector pGBAAS-1 and the pGBTOPPLA-1 vector (FIG. 2). The transformation and counterselection procedure results in a MARKER-GENE FREE PLA 1 strain containing multiple copies of the glucoamylase-porcine pancreatic phospholipase $A_2$ fusion protein encoding gene under control of the glucoamylase promoter.

*A. niger* Shake Flask Fermentations

*A. niger* strains are precultured in 20 ml preculture medium as described in the Examples: "*Aspergillus niger* shake flask fermentations" section of WO 99/32617. After overnight growth, 10 ml of this culture is transferred to Fermentation Medium (FM). Fermentation medium (FM) contains per liter: 82.5 g Glucose. 1H2O, 25 g Maldex 15 (Boom Meppel, Netherlands), 2 g Citric acid, 4.5 g NaH2PO4.1H2O, 9 g KH2PO4, 15 g (NH4)2SO4, 0.02 g ZnCl2, 0.1 g MnSO4.1H2O, 0.015 g CuSO4.5H2O, 0.015 g CoCl2.6H2O, 1 g MgSO4.7H2O, 0.1 g CaCl2.2H2O, 0.3 g FeSO4.7H2O, 30 g MES (2-[N-Morpholino]ethanesulfonic acid), pH=6.

Fermentation in FM is performed in 500 ml flasks with baffle with 100 ml fermentation broth at 34° C. and 170 rpm for the number of days indicated.

Enzyme Assays

PLA2 Phospholipase Activity

To determine phospholipase PLA2 activity (PLA2) in *Aspergillus niger* culture broth spectrophotometrically, an artificial substrate is used: 1,2-dithiodioctanoyl phophatidylcholine (diC8, substrate). PLA2 hydrolyses the sulphide bond at the A2 position, dissociating thio-octanoic acid. Thio-octanoic acid reacts with 4,4 dithiopyridine (color reagent, 4-DTDP), forming 4-thiopyridone. 4-Thiopyridone is in tautomeric equilibrium with 4-mercaptopyridine, which absorbs radiation having a wavelength of 334 nm. The extinction change at that wavelength is measured. One unit is the amount of enzyme that liberates of 1 nmol thio-octanoic acid from 1,2-dithiodioctanoyl phosphatidylcholine per minute at 37° C. and pH 4.0.

The substrate solution is prepared by dissolving 1 g diC8 crystals per 66 ml ethanol and add 264 ml acetate buffer. The acetate buffer comprises 0.1 M Acetate buffer pH 3.85 containing 0.2% Triton-X100. The colour reagent is a 11 mM 4,4-dithiodipyridine solution. It is prepared by weighting 5.0 mg 4,4-dithiodipyridine in a 2 ml eppendorf sample cup and dissolving in 1.00 ml ethanol. 1.00 ml of milli-Q water is added.

Proline Specific Endoprotease Activity

The proteolytic activity of the proline specific endoprotease is spectrophoto-metrically measured at 410 nm in time using CBZ-Gly(cine)-Pro(line)-pNA at 37° C. in a citrate/disodium phosphate buffer at pH 5. 1 U proline specific endoprotease is defined as the amount of enzyme which converts 1 μmol (micromol) CBZ-Gly(cine)-Pro(line)-pNA per min at pH 5 and 37° C. at the conditions described above.

Glucoamylase Activity Assay

The glucoamylase activity is determined using p-Nitrophenyl α-D-glucopyranoside (Sigma) as described in WO 98/46772.

Example 1

Cloning the sec61 Gene Encoding the Sec61 Translocation Channel in an Expression Vector Genomic DNA of *Aspergillus niger* strain WT 1 and *Penicillium chrysogenum* WT 4 are sequenced and analyzed. One gene with translated protein annotated as homologue to Sec61, is identified and named sec61. The genomic sequence of the *A. niger* sec61 locus, comprising the open reading frame (ORF) (with introns) and approximately 180 bp of the 5' untranslated region (UTR) and 327 bp of the 3' UTR, is shown in SEQ ID NO: 1. The genomic sequence of the *Penicillium chrysogenum* sec61 locus, comprising the open reading frame (ORF) (with introns) and approximately 12 bp of the 5' untranslated region (UTR) and 66 bp of the 3' UTR, is shown in SEQ ID NO: 7.

Genomic DNA from WT 1 is used as template in a PCR reaction using primers with SEQ ID NO: 13 and SEQ ID NO: 14 to amplify the wild-type sec61 gene and attach appropriate restriction sites. In parallel, the same experiment is performed using cDNA as template: the PCR reaction is performed using primers with SEQ ID NO: 14 and 15 to amplify the wild-type sec61 cDNA. All PCR reactions, cDNA synthesis, ligations and transformations are performed as described in: Molecular Cloning: A Laboratory Manual, Sambrook et al., New York: Cold Spring Harbour Press, 1989. Sequences of various independently amplified PCR fragments are determined by sequence analysis. The SEQ ID NO: 1 comprises the *A. niger* sec61 genomic sequence. The ORF of the cDNA sequence encoding the Sec61 protein of *A. niger* is provided as SEQ ID NO: 2. The translated amino acid sequence of the SEQ ID NO: 2 is assigned as SEQ ID NO: 3 and it represents the Sec61 protein of *A. niger* WT 1.

Genomic DNA from WT 4 is used as template in a PCR reaction using primers with SEQ ID NO: 10 and SEQ ID NO: 11 to amplify the wild-type sec61 gene and attach appropriate restriction sites. In parallel, the same experiment is performed using cDNA as template: the PCR reaction is performed using primers with SEQ ID NO: 11 and 12 to amplify the wild-type sec61 cDNA. Sequences of various independently amplified PCR fragments are determined by sequence analysis. The SEQ ID NO: 7 comprises the *Penicillium chrysogenum* sec61 genomic sequence. The ORF of the cDNA sequence encoding the Sec61 protein of *P. chrysogenum* is provided as SEQ ID NO: 8. The translated amino acid sequence of the SEQ ID NO: 8 is assigned as SEQ ID NO: 9 and it represents the Sec61 protein of *P. chrysogenum* WT 4.

Figure 3:
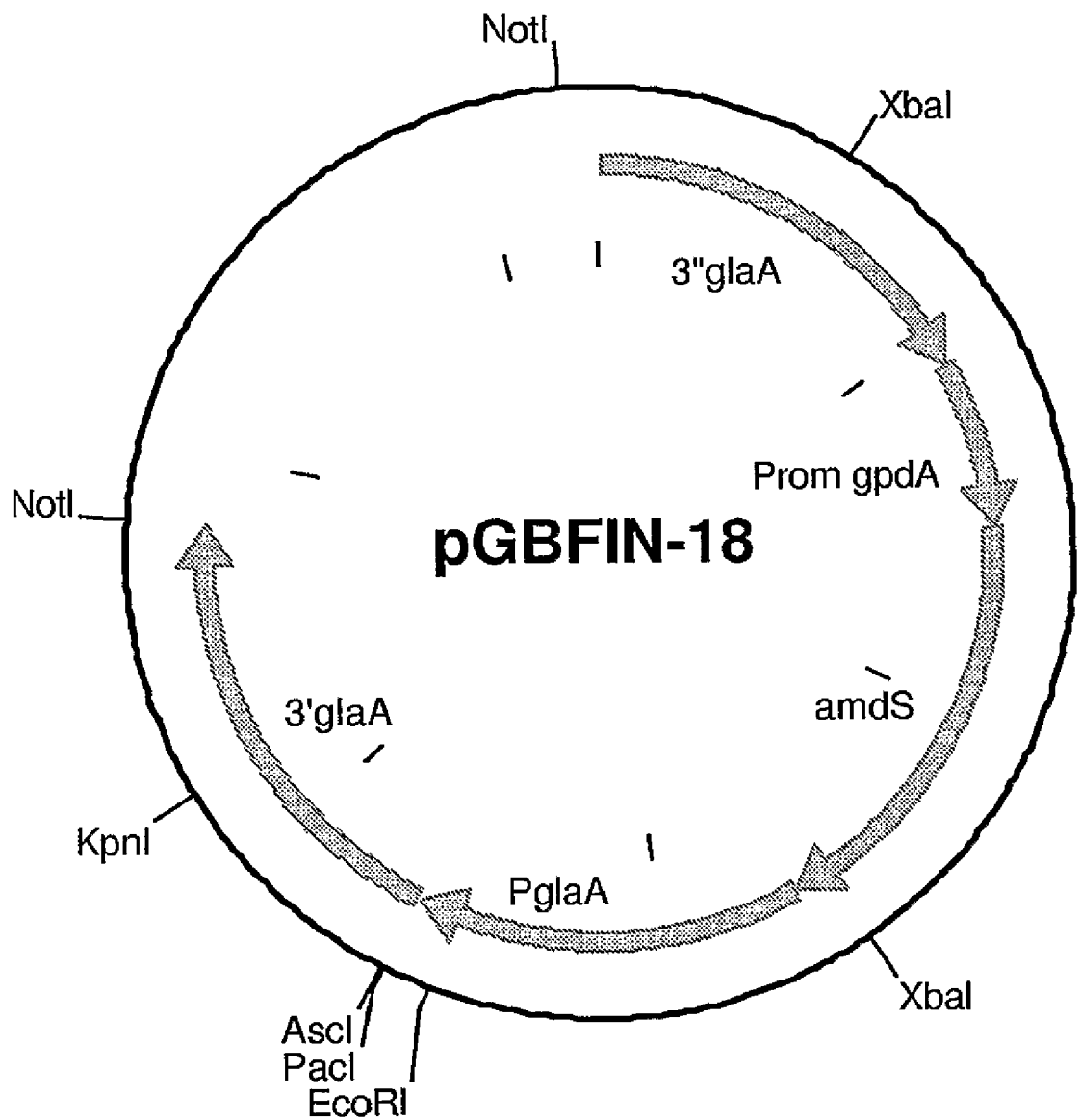
FIG. 3: Plasmid map of expression vector pGBFIN-18. Indicated are the glaA flanking regions relative to the glaA promoter with the unique SfiI and EcoRI cloning sites in the glucoamylase promoter followed by the PacI and AscI cloning sites. The *E. coli* DNA can be removed by digestion with restriction enzyme NotI, prior to transformation to the *A. niger* strains.
Figure 4:
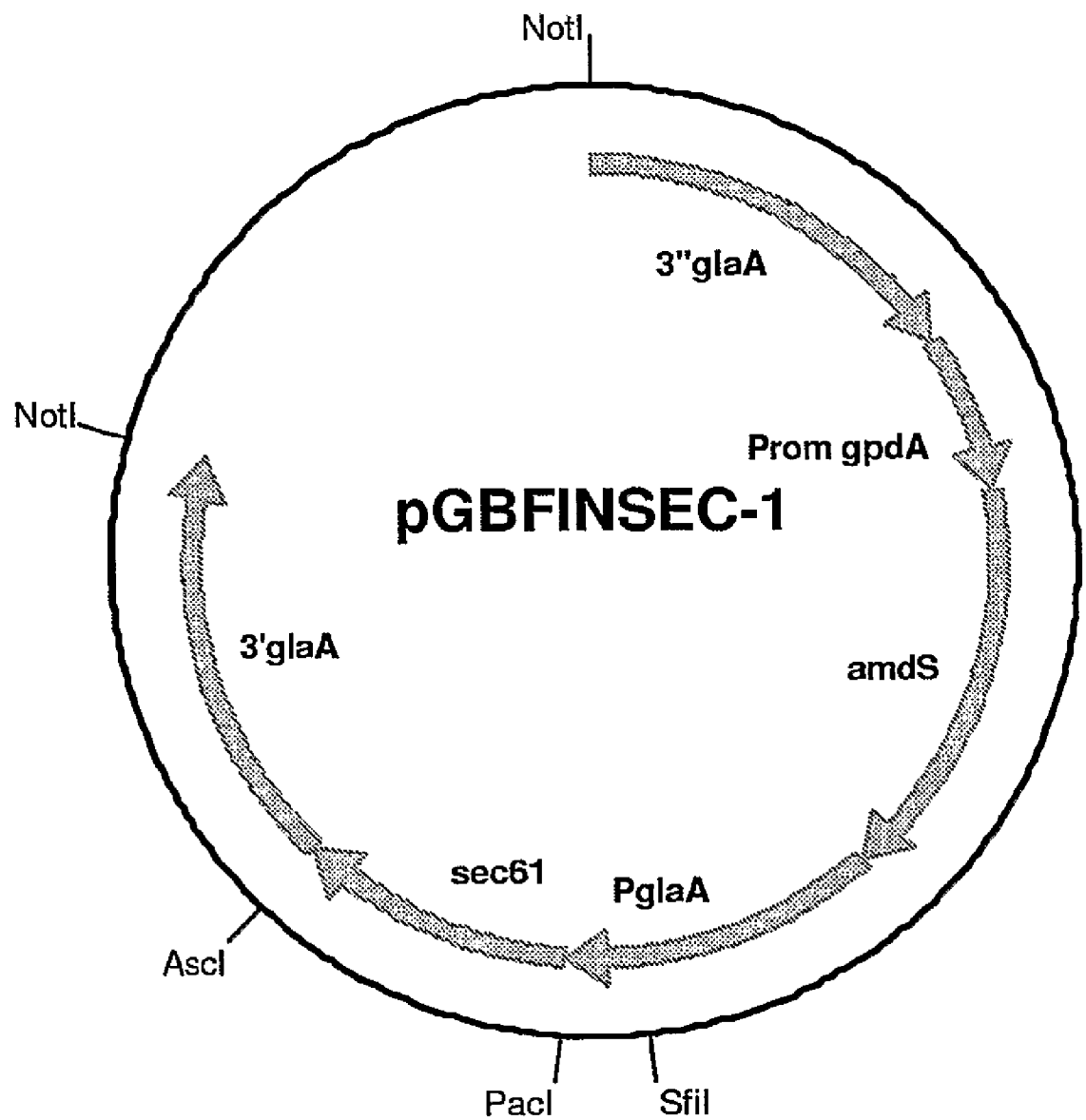
FIG. 4: Plasmid map of expression vector pGBFINSEC-1. Indicated are the glaA flanking regions relative to the glaA promoter and the *A. niger* genomic sec61 gene. The *E. coli* DNA can be removed by digestion with restriction enzyme NotI, prior to transformation of the *A. niger* strains.

The resulting PCR fragments, comprising the *A. niger* sec61 genomic DNA and cDNA sequences are cut with PacI and AscI according to the manufacturers instructions and ligated in a PacI, AscI linearized pGBFIN-18 *A. niger* expression vector (FIG. 3). The plasmid and the construction of the pGBFIN-18 vector is described in WO 99/32617. This resulted in the constructs pGBFINSEC-1 and pGBFINSEC-2, in which Sec61 is placed under control of the glaA promoter (see FIG. 4 for a map of pGBFINSEC-1).

The amdS gene under control of the constitutive gpdA promotor of *Aspergillus nidulans*, and also present in the pGBFIN-18-based *A. niger* expression vectors, can be used as selection marker and induced growth on acetamide as sole N-source (as described in Kelly, J. M., and Hynes, M. J. (1985). Transformation of *Aspergillus niger* by the amdS gene of *Aspergillus nidulans*. EMBO J. 4, 475-479).

Example 2

Construction of sec61* Encoding a Modified Sec61 Translocation Channel in a Gene-Replacement and Overexpression Vector Classical molecular biology techniques are used as described in Molecular Cloning: A Laboratory Manual, Sambrook et al., New York: Cold Spring Harbour Press, 1989. The general design of *A. niger* deletion vectors is described in EP635 574 and WO 98/46772.

A modified sec61 gene, called sec61* encoding a Sec61* protein in which Serine 376 is replaced by tryptophan, is constructed by sequence overlap extension PCR (SOE-PCR, as described in Gene. 1989 Apr. 15; 77(1):51-9. Ho S N, Hunt H D, Horton R M, Pullen J K, Pease L R "Site-directed mutagenesis by overlap extension using the polymerase chain reaction"). Using the oligonucleotides identified as SEQ ID NO: 18 and SEQ ID NO: 17, and genomic DNA of *A. niger* WT 1 as a template, the 5' region of 1.4 kb of the sec61 gene, identified as fragment A, is amplified by PCR. Additionally, an AscI restriction site is attached to the 5'-end of fragment A. Using oligonucleotides identified as SEQ ID NO: 16 and SEQ ID NO: 19 and genomic DNA of *A. niger* WT 1 as a template, the 3' region of 0.6 kb of the sec61 gene including 3'-UTR, identified as a fragment B, is amplified by PCR. Additionally, NotI and EcoRI restriction sites are attached to the 3'-end of fragment B. Both resulting fragments, A and B, are fused by SOE-PCR, oligonucleotides identified as SEQ ID NO: 18 and SEQ ID NO: 19 and fragments A and B; generating a 2 kb fragment C. This fragment C is cloned in pCR2.1-TOPO (Invitrogen), generating pCR_Sec61*. The sequence of the PCR generated fragment of pCR_Sec61* is confirmed and is provided as SEQ ID NO: 4. The coding sequence of the modified Sec61* protein is provided as SEQ ID NO: 5. The translated amino acid sequence of SEQ ID NO: 5 is assigned as SEQ ID NO: 6 and it represents the modified Sec61* protein.

Figure 5:
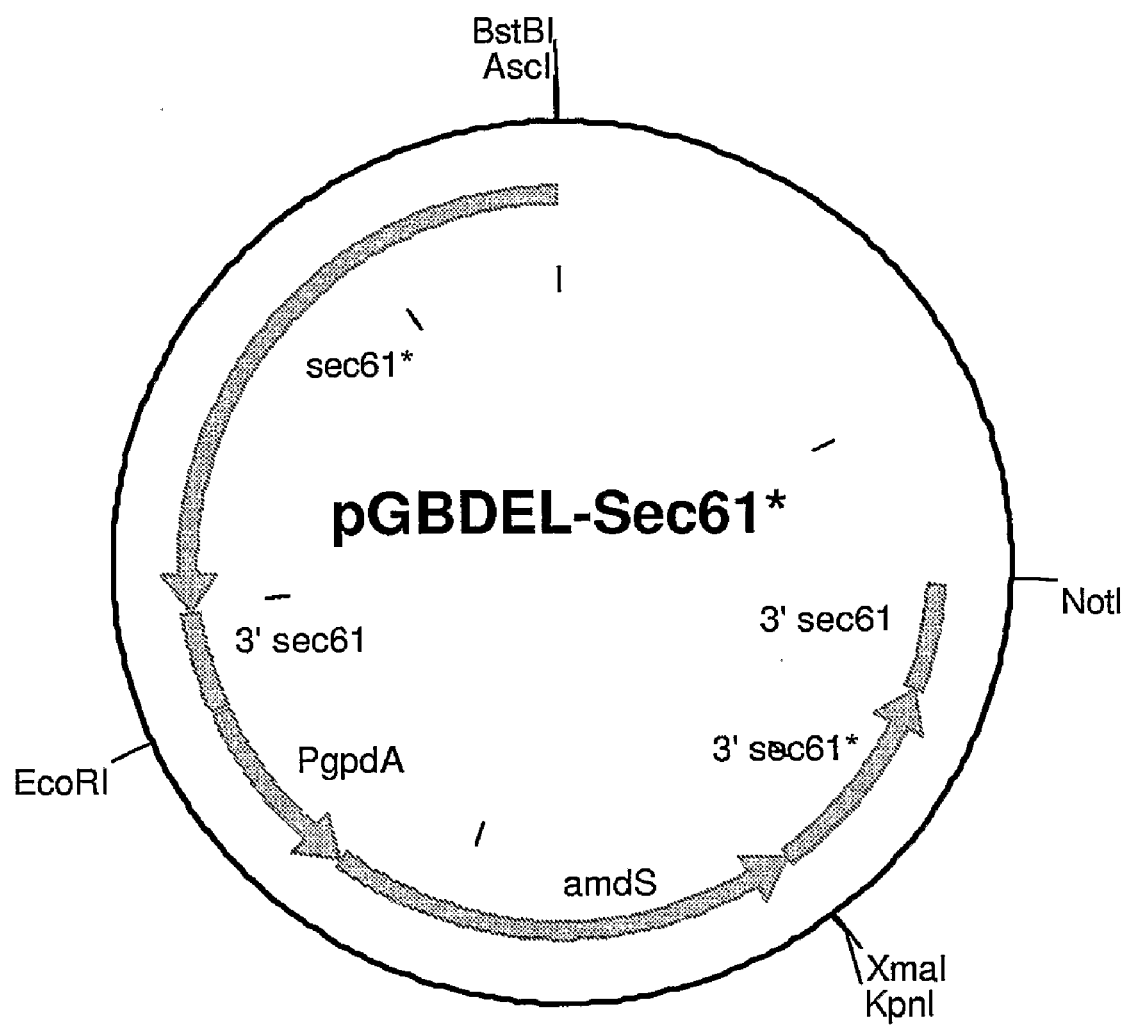
FIG. 5: Plasmid map of replacement vector pGBDEL-Sec61*. Indicated are a Sec61* mutant gene and a 3' Sec61* mutant gene fragment relative to the amdS marker. The *E. coli* DNA can be removed by digestion with restriction enzyme AscI and NotI, prior to transformation to the *A. niger* strains.

The vector pCR_Sec61* is digested with AscI and EcoRI and the sec61* fragment is introduced in an AscI and EcoRI digested vector pGBDEL, generating pGBDEL-1 (data not shown). Subsequently, vector pCR_Sec61* is digested with EcoRV and NotI and the 3' sec61* fragment is introduced in a SmaI and NotI digested vector pGBDEL-1, generating pGBDEL-SEC61* (FIG. 5).

Figure 6:
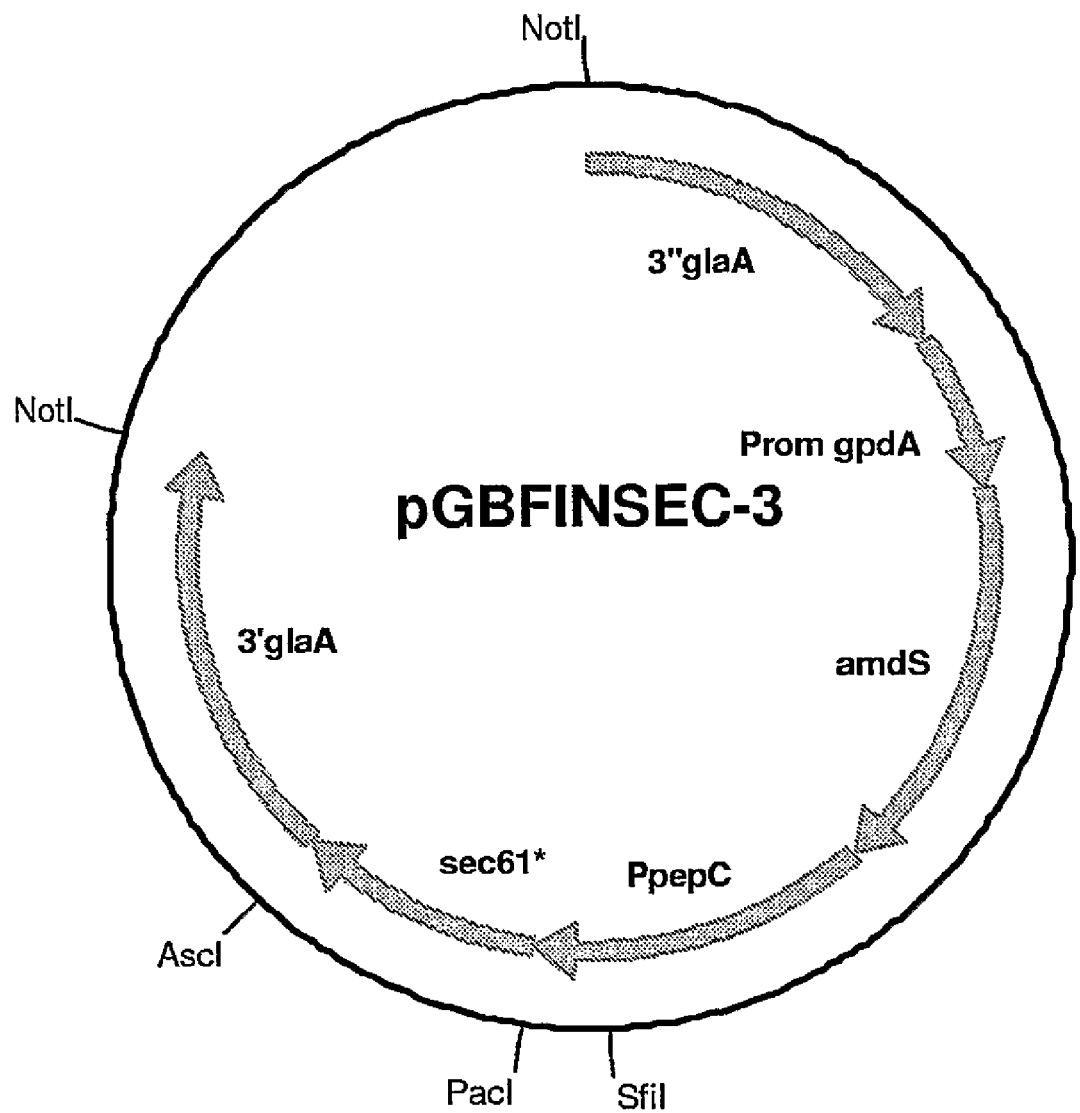
FIG. 6: Plasmid map of expression vector pGBFINSEC-3. Indicated are the glaA flanking regions relative to the glaApepC promoter and the modified sec61* gene. The *E. coli* DNA can be removed by digestion with restriction enzyme NotI, prior to transformation to the *A. niger* strains.

The vector pCR_Sec61* is used as template in a PCR reaction using primers with SEQ ID NO: 13 and SEQ ID NO: 14 to amplify the modified sec61* gene and attach appropriate restriction sites. The resulting PCR fragment, comprising the modified sec61* sequence is cut with PacI and AscI according to the manufacturers instructions and ligated in a PacI and AscI linearized pGBFIN *A. niger* expression vector, in which the PglaA promoter is replaced by the pepC promoter (Frederick G D, Rombouts P, Buxton F P (1993)— Cloning and characterisation of pepC, a gene encoding a serine protease from *Aspergillus niger*.—Gene 125(1): 57-64). This resulted in the pGBFINSEC-3 construct, in which a modified Sec61* gene is placed under control of the pepC promoter (FIG. 6).

Example 3

Fungal Host Cell Over-Expressing a Wild-Type sec61 and Modified sec61* Gene and Expressing a Modified sec61* Translocation Channel The amdS gene of *Aspergillus nidulans* placed under control of the constitutive gpdA promotor is used as selection marker as described in EP635 574. In principle, linear DNA of pGBFINSEC-1, pGBFINSEC-2, pGBFINSEC-3 and pGBDEL-SEC61* is isolated after digestion with the restriction enzymes indicated. *Aspergillus niger* PLA1 and EPO 1 strains are transformed and subsequent transformant selection on acetamide is carried out as described in WO 98/46772, EP635 574 and WO 99/32617. Subsequently, colonies are purified according standard procedures.

Growing colonies of the PLA1 and EPO 1 strains are diagnosed for copy numbers of the transforming SEC plasmids and no loss of pla2 and epo gene copies, respectively. Transformants of pGBFINSEC-1, pGBFINSEC-2 and pGBFINSEC-3 with similar estimated copy numbers and no loss of pla2 and epo gene copies are selected. A few transformants with a single copy (_A, _B, _C, _ . . . ) are selected. This resulted in a number of transformants over-expressing the wild-type genomic sec61 (pGBFINSEC-1), cDNA sec61 (pGBFINSEC-2) and modified sec61* gene (pGBFINSEC- 3). Transformants of the PLA 1 and EPO 1 strains are indicated as PLA_SEC1, PLA_SEC2, PLA_SEC3 and EPO_SEC1, EPO_SEC2, EPO_SEC3 respectively.

Figure 7:
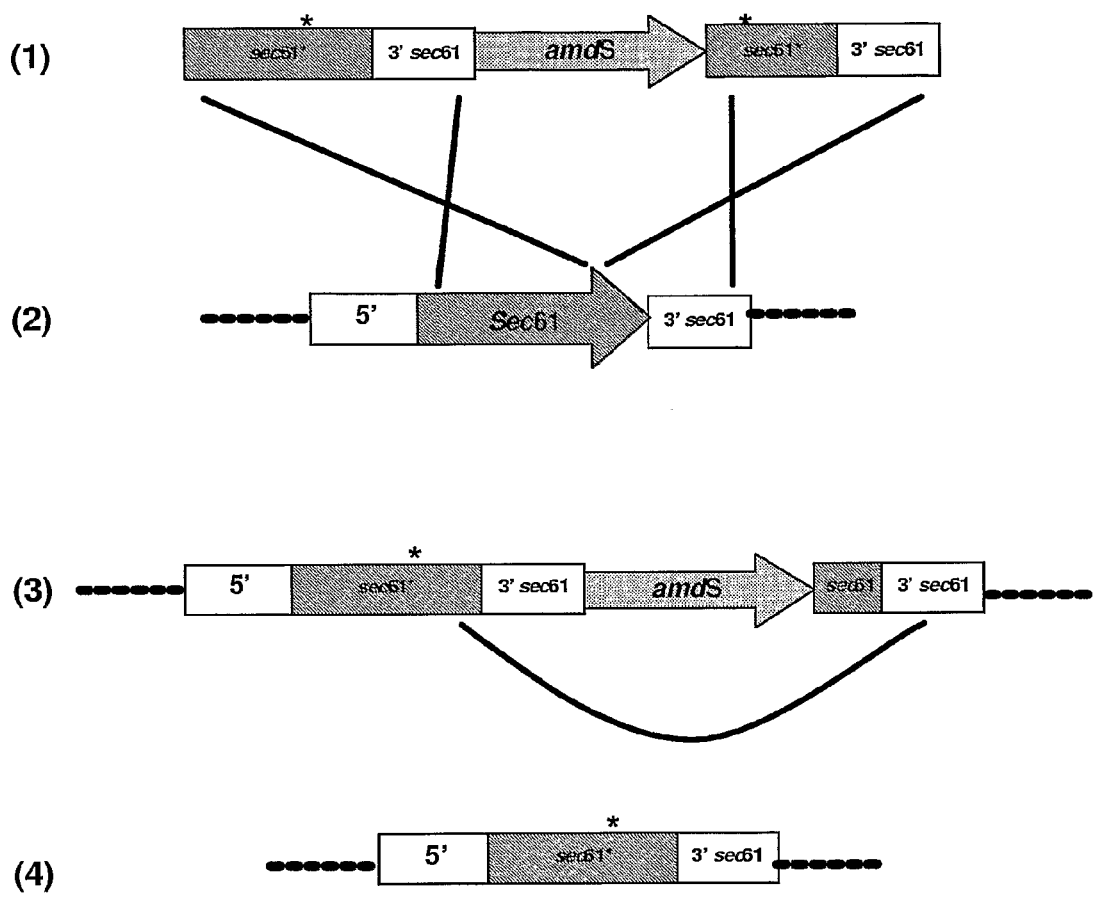
FIG. 7: Schematic presentation of the sec61 gene replacement. A linear DNA construct of pGBDEL-Sec61*, comprising the amdS selection marker flanked by homologous regions of the sec61 gene (1), integrates through double homologous recombination (X) at the genomic sec61 locus (2) and replaces the genomic sec61 gene copy (3) by the modified sec61* one. Subsequently, recombination over the direct repeats of (modified) sec61 sequences (U), removes the amdS marker, resulting in a gene replacement event of the sec61 gene by a modified sec61* gene (4). Both strains with (3) and without (4) the amdS marker have a functional modified sec61* gene

Transformants of the pGBDEL-SEC61* fragment that have integration into the genome at the sec61 locus have substituted the wild-type sec61 gene by the sec61* gene and amdS gene, as depicted in FIG. 7. Due to the used fragments and strategy for targeting, the substitution upon homologous recombination is not 100%. Therefore, purified pGBDEL-SEC61* transformants are diagnosed by two PCR reactions for homologous integration at the sec61 locus and substitution of the sec61 gene for the sec61* gene sequence. This substitution of sec61 with the sec61* gene is detectable by the first PCR amplification of a band using genomic DNA of pGBDEL-SEC61* transformants as template and using primers with SEQ ID NO: 20 and SEQ ID NO: 22 to amplify a modified sec61* gene at the sec61 locus. This replacement of sec61 with the sec61* gene is confirmed by a second PCR using genomic DNA of pGBDEL-SEC61* transformants as template and using primers with SEQ ID NO: 20 and SEQ ID NO: 21 to check the failure to amplify a wild-type sec61 gene. In addition, no loss of pla2 and epo gene copies, respectively is tested for. Subsequently, spores are plated on fluoro-acetamide media to select strains, which lost the amcS marker. Again, growing colonies are diagnosed by PCR for substitution of the sec61 gene for the sec61* gene sequence and no loss of pla2 or epo gene copies, as described above and candidate strains are tested by Southern analyses of the amdS containing transformant and the derived strains, which lost the amdS marker. Substitution of the sec61 gene for the sec61* gene is detectable by hybridization to sec61 probes of both strains, a~2.2 kb size increase of DNA fragments covering the entire locus in the amdS containing transformant and a wild-type fragment in the derived strain, which lost the amdS marker. Approximately 40% of the strains showed a homologous integration of pGBDEL-SEC61*, of which approximately 70% a substitution of the sec61 gene for the sec61* gene is detectable. Strains PLA_SEC61* and EPO_SEC61* are selected as representative strains with the sec61 gene replaced by a modified sec61* gene.

Additionally, *Aspergillus niger* PLA_SEC61* and EPO_SEC61* are transformed with linear DNA of pGBFIN-SEC-3 and subsequent transformant selection on acetamide and colony isolation is carried out as described above. Strains PLA_SEC61*_2 and EPO_SEC61*_2 are selected as representative strains for overexpression of a modified Sec61*, with the endogenous sec61 gene replaced by a modified sec61* gene, with an additional copy of a modified Sec61* gene under control of the strong glaA promoter and with no loss of pla2 or epo gene copies.

Example 4

Improvement of the Secretion of Proteins by the Obtained *Aspergillus niger* Strains Several *A. niger* WT 2 and EPO_SEC1, EPO_SEC2 and EPO_SEC3, EPO_SEC61* and EPO_SEC61*_2 transformants having equal copies of the pGBTOPEPO-1 construct are selected are selected to perform shake flask experiments. In addition, several *A. niger* WT 3 and PLA_SEC1, PLA_SEC2 and PLA_SEC3, PLA_SEC61* and PLA_SEC61*_2 transformants having equal copies of the pGBTOPPLA-1 construct are selected are selected to perform shake flask experiments. The shake flask experiments are performed in 100 ml of the Fermentation Medium (FM) as described in Experimental Procedures—"*A. niger* shake flask fermentations". The culture broth is collected during 7 days of the cultivation and the endoprotease and PLA2 activities are measured as described above.

Figure 8:
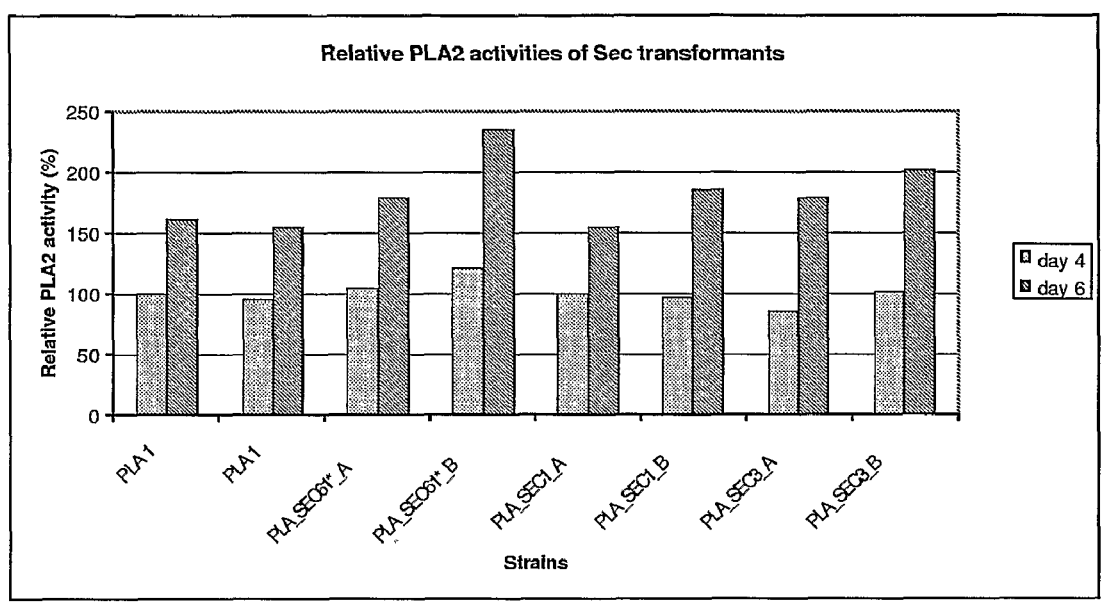
FIG. 8: Relative extra-cellular proline specific endoprotease activities of the EPO 1 strain transformed with various sec61 constructs. Samples are taken during several days of the fermentation. The expression of EPO 1 at day 3 is set as 100%.

FIG. 8 shows the relative proline specific endoprotease activities in transformants of the *A. niger* EPO strain with the same copy numbers. We conclude that over-expression of Sec61 and a modified Sec61* protein results in increased production of the endoprotease enzyme. Over-expression has been performed using the glucoamylase glaA and protease pepC promoter. In addition, over-expression of Sec61 with a genomic or cDNA construct or over-expression of a modified Sec61* with the endogenous sec61 gene still present in the genome results in increased production of the endoprotease enzyme.

Figure 9:
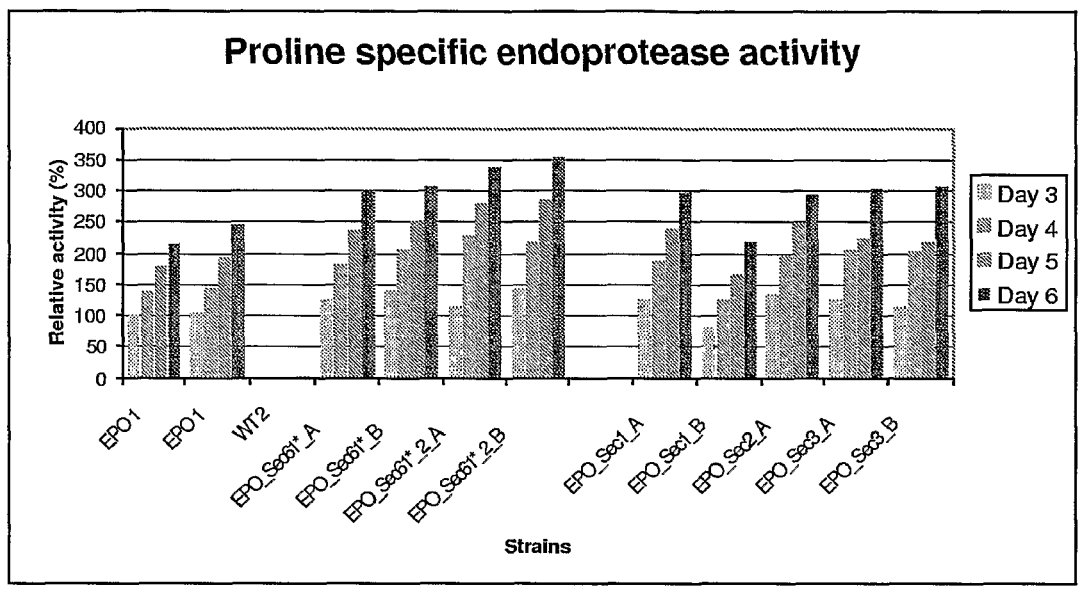
FIG. 9: Extra-cellular PLA2 activities of PLA 1 strain transformed with various sec61 constructs. Samples are taken during several days of the fermentation.
Figure 10:
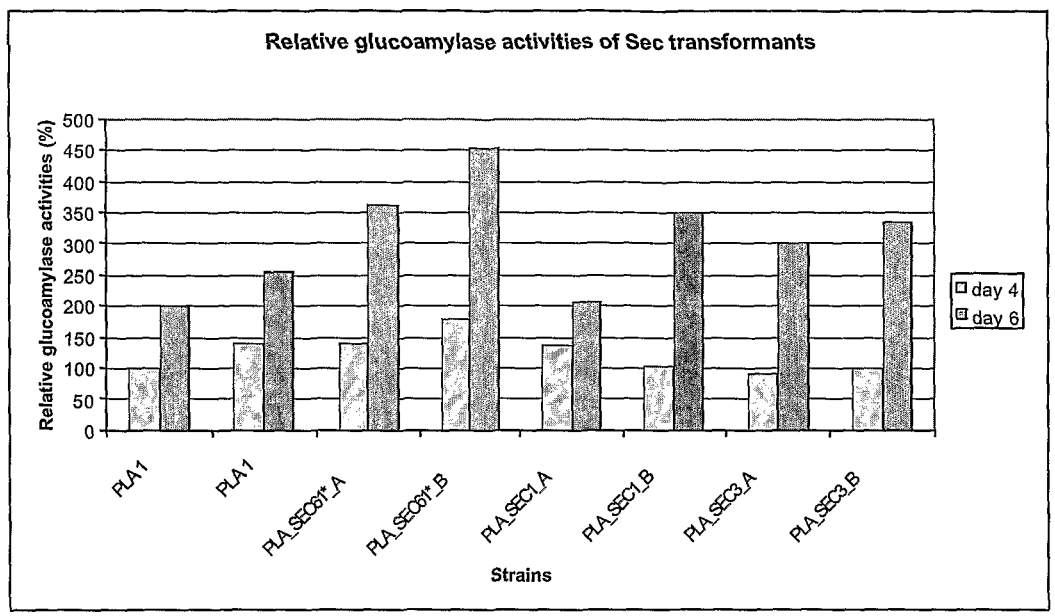
FIG. 10: Extra-cellular glucoamylase activities of PLA 1 strain transformed with various sec61 constructs. Strains and samples are identical as in FIG. 11. Samples are taken during several days of the fermentation.

These results show that sec61* and sec61 are excellent means to obtain improved production of polypeptides in fungal host cells. FIGS. 9 and 10 show the PLA2 and glucoamylase activities, respectively, as measured in transformants of *A. niger* WT 2, SEC1, SEC2, SEC3, SEC61* and SEC61*_2 and in an *A. niger* WT 2 pGBFIN-PLA2 transformant. It is clear that in the strain with the deleted wild type sec61 gene, a clear increase of the PLA2 activity is seen, as compared to the strain having the intact *A. niger* PLA 1 and PLA_SEC1, PLA_SEC3 and PLA_SEC61*, having equal copy numbers. We conclude that expression of a modified Sec61* protein results in increased production of both the heterologous phopholipase A2 as well as the homologous glucoamylase enzyme. Overexpression has been performed using the glucoamylase glaA and protease pepC promoter. Strains with no increased PLA2 and/or glucoamylase activity are shown to have lost copies during fermentation. Therefore, the expression per copy still improves with overexpression of Sec61. These results shows that manipulating the expression of sec61* and sec61 results in improved production of polypeptides in fungal host cells.

The invention claimed is:

1. An isolated polynucleotide encoding a polypeptide variant of SEQ ID NO:3, wherein:
   i) the polypeptide variant comprises an amino acid sequence having at least 90% amino acid sequence identity to the amino acid sequence of SEQ ID NO:3;
   ii) an amino acid residue corresponding to position(s) 373, 374, 375, 376, 377, 378, and/or 379 of SEQ ID NO:3 in the amino acid sequence of the polypeptide variant is substituted with a different amino acid relative to the corresponding amino acid of SEQ ID NO:3; and
   iii) the polypeptide variant has protein transport activity.

2. A polynucleotide according to claim 1, wherein the polynucleotide comprises SEQ ID NO:5 or a nucleotide sequence having at least 90% sequence identity to SEQ ID NO:2.

3. A nucleic acid construct or expression vector comprising the polynucleotide of claim 1, said polynucleotide being operably linked to one or more control sequences which direct the expression of the polypeptide in a suitable host cell.

4. A nucleic acid construct or expression vector according to claim 3, wherein the control sequences comprise a promoter, and transcriptional and translational stop signals.

5. A host cell transformed with the polynucleotide according to claim 1.

6. A host cell according to claim 5 that is a filamentous fungal cell.

7. A host cell according to claim 6, wherein the filamentous fungal cell belongs to a species selected from the group consisting of an *Aspergillus, Penicillium* or *Trichoderma* species.

8. A host cell according to claim 7, wherein the filamentous fungal cell belongs to species of *Aspergillus niger* or *Aspergillus oryzae*.

9. A host cell according to claim 5, wherein the host cell additionally comprises a polynucleotide or an expression vector comprising a nucleic acid sequence encoding a polypeptide of interest.

10. A process for producing a polypeptide of interest comprising culturing the host cell of claim 5 under conditions conducive to expression of the polypeptide of interest and optionally recovering the polypeptide of interest form the culture broth.

11. A polynucleotide according to claim 1, wherein the polynucleotide comprises a nucleotide sequence having at least 90% sequence identity to SEQ ID NO:2.

12. A polynucleotide according to claim 1, wherein the polynucleotide comprises a nucleotide sequence having at least 95% sequence identity to SEQ ID NO:2.

13. A polynucleotide according to claim 1, wherein the amino acid residue corresponding to position 376 of SEQ ID NO:3 in the amino acid sequence of the polypeptide variant is substituted with a different amino acid relative to the corresponding amino acid of SEQ ID NO:3.

14. A polynucleotide according to claim 1, wherein the amino acid residue corresponding to position 376 of SEQ ID NO:3 in the amino acid sequence of the polypeptide variant is tryptophan, phenylalanine, tyrosine or histidine.

15. A polynucleotide according to claim 1, wherein the amino acid residue corresponding to position 376 of SEQ ID NO:3 in the amino acid sequence of the polypeptide variant is tryptophan.

16. A polynucleotide according to claim 1, wherein the amino acid sequence of the polypeptide variant is SEQ ID NO:6.

17. A host cell transformed with the nucleic acid construct or expression vector according to claim 3.

18. A process for producing a polypeptide of interest comprising culturing the host cell of claim 17 under conditions conducive to expression of the polypeptide of interest and optionally recovering the polypeptide of interest form the culture broth.

* * * * *